US011986630B2

(12) United States Patent
Lee et al.

(10) Patent No.: US 11,986,630 B2
(45) Date of Patent: May 21, 2024

(54) DUAL HORMONE DELIVERY SYSTEM FOR REDUCING IMPENDING HYPOGLYCEMIA AND/OR HYPERGLYCEMIA RISK

(71) Applicant: Insulet Corporation, Acton, MA (US)

(72) Inventors: Joon Bok Lee, Acton, MA (US); Ashutosh Zade, San Diego, CA (US); Jason O'Connor, Acton, MA (US); Trang Ly, Concord, MA (US); Yibin Zheng, Hartland, WI (US); Connor Gullifer, Brighton, MA (US); Kyle Grover, Watertown, MA (US)

(73) Assignee: INSULET CORPORATION, Acton, MA (US)

( * ) Notice: Subject to any disclaimer, the term of this patent is extended or adjusted under 35 U.S.C. 154(b) by 729 days.

(21) Appl. No.: 16/788,892

(22) Filed: Feb. 12, 2020

(65) Prior Publication Data

US 2021/0244880 A1  Aug. 12, 2021

(51) Int. Cl.
*A61M 5/172* (2006.01)
*G16H 20/17* (2018.01)

(52) U.S. Cl.
CPC .......... *A61M 5/1723* (2013.01); *G16H 20/17* (2018.01); *A61M 2202/07* (2013.01);
(Continued)

(58) Field of Classification Search
CPC ............ A61M 5/1723; A61M 2205/52; A61M 2230/201; G16H 20/17
See application file for complete search history.

(56) References Cited

U.S. PATENT DOCUMENTS 303,013 A   8/1884  Horton
2,797,149 A  6/1957  Skeggs
(Continued)

FOREIGN PATENT DOCUMENTS

AU   2015200834 A1   3/2015
AU   2015301146 A1   3/2017
(Continued)

OTHER PUBLICATIONS

US 5,954,699 A, 09/1999, Jost et al. (withdrawn)
(Continued)

*Primary Examiner* — Phillip A Gray
(74) *Attorney, Agent, or Firm* — GOODWIN PROCTER LLP

(57) ABSTRACT

The exemplary embodiments attempt to identify impending hypoglycemia and/or hyperglycemia and take measures to prevent the hypoglycemia or hyperglycemia. Exemplary embodiments may provide a drug delivery system for delivering insulin and glucagon as needed by a user of the drug delivery system. The drug delivery system may deploy a control system that controls the automated delivery of insulin and glucagon to a patient by the drug delivery system. The control system seeks among other goals to avoid the user experiencing hypoglycemia or hyperglycemia. The control system may employ a clinical decision support algorithm as is described below to control delivery of insulin and glucagon to reduce the risk of hypoglycemia or hyperglycemia and to provide alerts to the user when needed. The control system assesses whether the drug delivery system can respond enough to avoid hypoglycemia or hyperglycemia and generates alerts when manual action is needed to avoid hypoglycemia or hyperglycemia.

12 Claims, 15 Drawing Sheets

(52) U.S. Cl.
CPC . *A61M 2205/18* (2013.01); *A61M 2205/3569* (2013.01); *A61M 2205/50* (2013.01); *A61M 2205/502* (2013.01); *A61M 2205/52* (2013.01); *A61M 2205/581* (2013.01); *A61M 2205/583* (2013.01); *A61M 2230/201* (2013.01)

(56) References Cited

U.S. PATENT DOCUMENTS

| | | |
|---|---|---|
| 3,631,847 A | 1/1972 | Hobbs |
| 3,634,039 A | 1/1972 | Brondy |
| 3,812,843 A | 5/1974 | Wootten et al. |
| 3,841,328 A | 10/1974 | Jensen |
| 3,963,380 A | 6/1976 | Thomas, Jr. et al. |
| 4,055,175 A | 10/1977 | Clemens et al. |
| 4,146,029 A | 3/1979 | Ellinwood, Jr. |
| 4,151,845 A | 5/1979 | Clemens |
| 4,245,634 A | 1/1981 | Albisser et al. |
| 4,368,980 A | 1/1983 | Aldred et al. |
| 4,373,527 A | 2/1983 | Fischell |
| 4,403,984 A | 9/1983 | Ash et al. |
| 4,464,170 A | 8/1984 | Clemens et al. |
| 4,469,481 A | 9/1984 | Kobayashi |
| 4,475,901 A | 10/1984 | Kraegen et al. |
| 4,526,568 A | 7/1985 | Clemens et al. |
| 4,526,569 A | 7/1985 | Bernardi |
| 4,529,401 A | 7/1985 | Leslie et al. |
| 4,559,033 A | 12/1985 | Stephen et al. |
| 4,559,037 A | 12/1985 | Franetzki et al. |
| 4,573,968 A | 3/1986 | Parker |
| 4,624,661 A | 11/1986 | Arimond |
| 4,633,878 A | 1/1987 | Bombardieri |
| 4,657,529 A | 4/1987 | Prince et al. |
| 4,685,903 A | 8/1987 | Cable et al. |
| 4,731,726 A | 3/1988 | Allen, III |
| 4,743,243 A | 5/1988 | Vaillancourt |
| 4,755,173 A | 7/1988 | Konopka et al. |
| 4,781,688 A | 11/1988 | Thoma et al. |
| 4,781,693 A | 11/1988 | Martinez et al. |
| 4,808,161 A | 2/1989 | Kamen |
| 4,854,170 A | 8/1989 | Brimhall et al. |
| 4,886,499 A | 12/1989 | Cirelli et al. |
| 4,900,292 A | 2/1990 | Berry et al. |
| 4,919,596 A | 4/1990 | Slate et al. |
| 4,925,444 A | 5/1990 | Orkin et al. |
| 4,940,527 A | 7/1990 | Kazlauskas et al. |
| 4,975,581 A | 12/1990 | Robinson et al. |
| 4,976,720 A | 12/1990 | Machold et al. |
| 4,981,140 A | 1/1991 | Wyatt |
| 4,994,047 A | 2/1991 | Walker et al. |
| 5,007,286 A | 4/1991 | Malcolm et al. |
| 5,097,834 A | 3/1992 | Skrabal |
| 5,102,406 A | 4/1992 | Arnold |
| 5,109,850 A | 5/1992 | Blanco et al. |
| 5,125,415 A | 6/1992 | Bell |
| 5,134,079 A | 7/1992 | Cusack et al. |
| 5,153,827 A | 10/1992 | Coutre et al. |
| 5,165,406 A | 11/1992 | Wong |
| 5,176,662 A | 1/1993 | Bartholomew et al. |
| 5,178,609 A | 1/1993 | Ishikawa |
| 5,207,642 A | 5/1993 | Orkin et al. |
| 5,232,439 A | 8/1993 | Campbell et al. |
| 5,237,993 A | 8/1993 | Skrabal |
| 5,244,463 A | 9/1993 | Cordner, Jr. et al. |
| 5,257,980 A | 11/1993 | Van Antwerp et al. |
| 5,273,517 A | 12/1993 | Barone et al. |
| 5,281,808 A | 1/1994 | Kunkel |
| 5,299,571 A | 4/1994 | Mastrototaro |
| 5,308,982 A | 5/1994 | Ivaldi et al. |
| 5,342,298 A | 8/1994 | Michaels et al. |
| 5,377,674 A | 1/1995 | Kuestner |
| 5,380,665 A | 1/1995 | Cusack et al. |
| 5,385,539 A | 1/1995 | Maynard |
| 5,389,078 A | 2/1995 | Zalesky et al. |
| 5,411,889 A | 5/1995 | Hoots et al. |
| 5,421,812 A | 6/1995 | Langley et al. |
| 5,468,727 A | 11/1995 | Phillips et al. |
| 5,505,709 A | 4/1996 | Funderburk et al. |
| 5,505,828 A | 4/1996 | Wong et al. |
| 5,507,288 A | 4/1996 | Bocker et al. |
| 5,533,389 A | 7/1996 | Kamen et al. |
| 5,558,640 A | 9/1996 | Pfeiler et al. |
| 5,569,186 A | 10/1996 | Lord et al. |
| 5,584,813 A | 12/1996 | Livingston et al. |
| 5,609,572 A | 3/1997 | Lang |
| 5,665,065 A | 9/1997 | Colman et al. |
| 5,678,539 A | 10/1997 | Schubert et al. |
| 5,685,844 A | 11/1997 | Marttila |
| 5,685,859 A | 11/1997 | Kornerup |
| 5,693,018 A | 12/1997 | Kriesel et al. |
| 5,697,899 A | 12/1997 | Hillman et al. |
| 5,700,695 A | 12/1997 | Yassinzadeh et al. |
| 5,703,364 A | 12/1997 | Rosenthal |
| 5,714,123 A | 2/1998 | Sohrab |
| 5,716,343 A | 2/1998 | Kriesel et al. |
| 5,722,397 A | 3/1998 | Eppstein |
| 5,741,228 A | 4/1998 | Lambrecht et al. |
| 5,746,217 A | 5/1998 | Erickson et al. |
| 5,755,682 A | 5/1998 | Knudson et al. |
| 5,758,643 A | 6/1998 | Wong et al. |
| 5,800,405 A | 9/1998 | McPhee |
| 5,800,420 A | 9/1998 | Gross et al. |
| 5,801,057 A | 9/1998 | Smart et al. |
| 5,804,048 A | 9/1998 | Wong et al. |
| 5,817,007 A | 10/1998 | Fodgaard et al. |
| 5,820,622 A | 10/1998 | Gross et al. |
| 5,823,951 A | 10/1998 | Messerschmidt |
| 5,840,020 A | 11/1998 | Heinonen et al. |
| 5,848,991 A | 12/1998 | Gross et al. |
| 5,851,197 A | 12/1998 | Marano et al. |
| 5,858,005 A | 1/1999 | Kriesel |
| 5,865,806 A | 2/1999 | Howell |
| 5,871,470 A | 2/1999 | McWha |
| 5,879,310 A | 3/1999 | Sopp et al. |
| 5,902,253 A | 5/1999 | Pfeiffer et al. |
| 5,931,814 A | 8/1999 | Alex et al. |
| 5,932,175 A | 8/1999 | Knute et al. |
| 5,935,099 A | 8/1999 | Peterson et al. |
| 5,947,911 A | 9/1999 | Wong et al. |
| 5,971,941 A | 10/1999 | Simons et al. |
| 5,993,423 A | 11/1999 | Choi |
| 5,997,501 A | 12/1999 | Gross et al. |
| 6,017,318 A | 1/2000 | Gauthier et al. |
| 6,024,539 A | 2/2000 | Blomquist |
| 6,032,059 A | 2/2000 | Henning et al. |
| 6,036,924 A | 3/2000 | Simons et al. |
| 6,040,578 A | 3/2000 | Malin et al. |
| 6,049,727 A | 4/2000 | Crothall |
| 6,050,978 A | 4/2000 | Orr et al. |
| 6,058,934 A | 5/2000 | Sullivan |
| 6,066,103 A | 5/2000 | Duchon et al. |
| 6,071,292 A | 6/2000 | Makower et al. |
| 6,072,180 A | 6/2000 | Kramer et al. |
| 6,077,055 A | 6/2000 | Vilks |
| 6,090,092 A | 7/2000 | Fowles et al. |
| 6,101,406 A | 8/2000 | Hacker et al. |
| 6,102,872 A | 8/2000 | Doneen et al. |
| 6,115,673 A | 9/2000 | Malin et al. |
| 6,123,827 A | 9/2000 | Wong et al. |
| 6,124,134 A | 9/2000 | Stark |
| 6,126,637 A | 10/2000 | Kriesel et al. |
| 6,128,519 A | 10/2000 | Say |
| 6,142,939 A | 11/2000 | Eppstein et al. |
| 6,143,164 A | 11/2000 | Heller et al. |
| 6,157,041 A | 12/2000 | Thomas et al. |
| 6,161,028 A | 12/2000 | Braig et al. |
| 6,162,639 A | 12/2000 | Douglas |
| 6,196,046 B1 | 3/2001 | Braig et al. |
| 6,200,287 B1 | 3/2001 | Keller et al. |
| 6,200,338 B1 | 3/2001 | Solomon et al. |
| 6,214,629 B1 | 4/2001 | Freitag et al. |
| 6,226,082 B1 | 5/2001 | Roe |
| 6,244,776 B1 | 6/2001 | Wiley |
| 6,261,065 B1 | 7/2001 | Nayak et al. |
| 6,262,798 B1 | 7/2001 | Shepherd et al. |

(56) References Cited

U.S. PATENT DOCUMENTS

| | | |
|---|---|---|
| 6,270,455 B1 | 8/2001 | Brown |
| 6,271,045 B1 | 8/2001 | Douglas et al. |
| 6,280,381 B1 | 8/2001 | Malin et al. |
| 6,285,448 B1 | 9/2001 | Kuenstner |
| 6,309,370 B1 | 10/2001 | Haim et al. |
| 6,312,888 B1 | 11/2001 | Wong et al. |
| 6,334,851 B1 | 1/2002 | Hayes et al. |
| 6,375,627 B1 | 4/2002 | Mauze et al. |
| 6,379,301 B1 | 4/2002 | Worthington et al. |
| 6,402,689 B1 | 6/2002 | Scarantino et al. |
| 6,470,279 B1 | 10/2002 | Samsoondar |
| 6,475,196 B1 | 11/2002 | Vachon |
| 6,477,901 B1 | 11/2002 | Tadigadapa et al. |
| 6,484,044 B1 | 11/2002 | Lilienfeld-Toal |
| 6,491,656 B1 | 12/2002 | Morris |
| 6,512,937 B2 | 1/2003 | Blank et al. |
| 6,525,509 B1 | 2/2003 | Petersson et al. |
| 6,528,809 B1 | 3/2003 | Thomas et al. |
| 6,540,672 B1 | 4/2003 | Simonsen et al. |
| 6,544,212 B2 | 4/2003 | Galley et al. |
| 6,546,268 B1 | 4/2003 | Ishikawa et al. |
| 6,546,269 B1 | 4/2003 | Kurnik |
| 6,553,841 B1 | 4/2003 | Blouch |
| 6,554,798 B1 | 4/2003 | Mann et al. |
| 6,556,850 B1 | 4/2003 | Braig et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,562,014 B2 | 5/2003 | Lin et al. |
| 6,569,125 B2 | 5/2003 | Jepson et al. |
| 6,572,542 B1 | 6/2003 | Houben et al. |
| 6,572,545 B2 | 6/2003 | Knobbe et al. |
| 6,574,490 B2 | 6/2003 | Abbink et al. |
| 6,575,905 B2 | 6/2003 | Knobbe et al. |
| 6,580,934 B1 | 6/2003 | Braig et al. |
| 6,618,603 B2 | 9/2003 | Varalli et al. |
| 6,633,772 B2 | 10/2003 | Ford et al. |
| 6,645,142 B2 | 11/2003 | Braig et al. |
| 6,653,091 B1 | 11/2003 | Dunn et al. |
| 6,662,030 B2 | 12/2003 | Khalil et al. |
| 6,669,663 B1 | 12/2003 | Thompson |
| 6,678,542 B2 | 1/2004 | Braig et al. |
| 6,699,221 B2 | 3/2004 | Vaillancourt |
| 6,718,189 B2 | 4/2004 | Rohrscheib et al. |
| 6,721,582 B2 | 4/2004 | Trepagnier et al. |
| 6,728,560 B2 | 4/2004 | Kollias et al. |
| 6,740,059 B2 | 5/2004 | Flaherty |
| 6,740,072 B2 | 5/2004 | Starkweather et al. |
| 6,751,490 B2 | 6/2004 | Esenaliev et al. |
| 6,758,835 B2 | 7/2004 | Close et al. |
| 6,780,156 B2 | 8/2004 | Haueter et al. |
| 6,810,290 B2 | 10/2004 | Lebel et al. |
| 6,837,858 B2 | 1/2005 | Cunningham et al. |
| 6,837,988 B2 | 1/2005 | Leong et al. |
| 6,846,288 B2 | 1/2005 | Nagar et al. |
| 6,862,534 B2 | 3/2005 | Sterling et al. |
| 6,865,408 B1 | 3/2005 | Abbink et al. |
| 6,890,291 B2 | 5/2005 | Robinson et al. |
| 6,936,029 B2 | 8/2005 | Mann et al. |
| 6,949,081 B1 | 9/2005 | Chance |
| 6,958,809 B2 | 10/2005 | Sterling et al. |
| 6,989,891 B2 | 1/2006 | Braig et al. |
| 6,990,366 B2 | 1/2006 | Say et al. |
| 7,008,404 B2 | 3/2006 | Nakajima |
| 7,009,180 B2 | 3/2006 | Sterling et al. |
| 7,016,713 B2 | 3/2006 | Gardner et al. |
| 7,018,360 B2 | 3/2006 | Flaherty et al. |
| 7,025,743 B2 | 4/2006 | Mann et al. |
| 7,025,744 B2 | 4/2006 | Utterberg et al. |
| 7,027,848 B2 | 4/2006 | Robinson et al. |
| 7,043,288 B2 | 5/2006 | Davis, III et al. |
| 7,060,059 B2 | 6/2006 | Keith et al. |
| 7,061,593 B2 | 6/2006 | Braig et al. |
| 7,096,124 B2 | 8/2006 | Sterling et al. |
| 7,115,205 B2 | 10/2006 | Robinson et al. |
| 7,128,727 B2 | 10/2006 | Flaherty et al. |
| 7,139,593 B2 | 11/2006 | Kavak et al. |
| 7,139,598 B2 | 11/2006 | Hull et al. |
| 7,144,384 B2 | 12/2006 | Gorman et al. |
| 7,171,252 B1 | 1/2007 | Scarantino et al. |
| 7,190,988 B2 | 3/2007 | Say et al. |
| 7,204,823 B2 | 4/2007 | Estes et al. |
| 7,248,912 B2 | 7/2007 | Gough et al. |
| 7,267,665 B2 | 9/2007 | Steil et al. |
| 7,271,912 B2 | 9/2007 | Sterling et al. |
| 7,278,983 B2 | 10/2007 | Ireland et al. |
| 7,291,107 B2 | 11/2007 | Hellwig et al. |
| 7,291,497 B2 | 11/2007 | Holmes et al. |
| 7,303,549 B2 | 12/2007 | Flaherty et al. |
| 7,303,622 B2 | 12/2007 | Loch et al. |
| 7,303,922 B2 | 12/2007 | Jeng et al. |
| 7,354,420 B2 | 4/2008 | Steil et al. |
| 7,388,202 B2 | 6/2008 | Sterling et al. |
| 7,402,153 B2 | 7/2008 | Steil et al. |
| 7,404,796 B2 | 7/2008 | Ginsberg |
| 7,429,255 B2 | 9/2008 | Thompson |
| 7,460,130 B2 | 12/2008 | Salganicoff |
| 7,481,787 B2 | 1/2009 | Gable et al. |
| 7,491,187 B2 | 2/2009 | Van Den Berghe et al. |
| 7,500,949 B2 | 3/2009 | Gottlieb et al. |
| 7,509,156 B2 | 3/2009 | Flanders |
| 7,547,281 B2 | 6/2009 | Hayes et al. |
| 7,569,030 B2 | 8/2009 | Lebel et al. |
| 7,608,042 B2 | 10/2009 | Goldberger et al. |
| 7,651,845 B2 | 1/2010 | Doyle, III et al. |
| 7,680,529 B2 | 3/2010 | Kroll |
| 7,734,323 B2 | 6/2010 | Blomquist et al. |
| 7,766,829 B2 | 8/2010 | Sloan et al. |
| 7,785,258 B2 | 8/2010 | Braig et al. |
| 7,806,854 B2 | 10/2010 | Damiano et al. |
| 7,806,886 B2 | 10/2010 | Kanderian, Jr. et al. |
| 7,918,825 B2 | 4/2011 | OConnor et al. |
| 7,946,985 B2 | 5/2011 | Mastrototaro et al. |
| 7,972,296 B2 | 7/2011 | Braig et al. |
| 8,221,345 B2 | 7/2012 | Blomquist |
| 8,251,907 B2 | 8/2012 | Sterling et al. |
| 8,449,524 B2 | 5/2013 | Braig et al. |
| 8,452,359 B2 | 5/2013 | Rebec et al. |
| 8,454,576 B2 | 6/2013 | Mastrototaro et al. |
| 8,467,980 B2 | 6/2013 | Campbell et al. |
| 8,478,557 B2 | 7/2013 | Hayter et al. |
| 8,547,239 B2 | 10/2013 | Peatfield et al. |
| 8,597,274 B2 | 12/2013 | Sloan et al. |
| 8,622,988 B2 | 1/2014 | Hayter |
| 8,810,394 B2 | 8/2014 | Kalpin |
| 9,061,097 B2 | 6/2015 | Holt et al. |
| 9,171,343 B1 | 10/2015 | Fischell et al. |
| 9,233,204 B2 | 1/2016 | Booth et al. |
| 9,486,571 B2 | 11/2016 | Rosinko |
| 9,579,456 B2 | 2/2017 | Budiman et al. |
| 9,743,224 B2 | 8/2017 | San Vicente et al. |
| 9,907,515 B2 | 3/2018 | Doyle, III et al. |
| 9,980,140 B1 | 5/2018 | Spencer et al. |
| 9,984,773 B2 | 5/2018 | Gondhalekar et al. |
| 10,248,839 B2 | 4/2019 | Levy et al. |
| 10,335,464 B1 | 7/2019 | Michelich et al. |
| 10,583,250 B2 | 3/2020 | Mazlish et al. |
| 10,737,024 B2 | 8/2020 | Schmid |
| 10,987,468 B2 | 4/2021 | Mazlish et al. |
| 11,197,964 B2 | 12/2021 | Sjolund et al. |
| 11,260,169 B2 | 3/2022 | Estes |
| 2001/0021803 A1 | 9/2001 | Blank et al. |
| 2001/0034023 A1 | 10/2001 | Stanton, Jr. et al. |
| 2001/0034502 A1 | 10/2001 | Moberg et al. |
| 2001/0051377 A1 | 12/2001 | Hammer et al. |
| 2001/0053895 A1 | 12/2001 | Vaillancourt |
| 2002/0010401 A1 | 1/2002 | Bushmakin et al. |
| 2002/0010423 A1 | 1/2002 | Gross et al. |
| 2002/0016568 A1 | 2/2002 | Lebel et al. |
| 2002/0040208 A1 | 4/2002 | Flaherty et al. |
| 2002/0123740 A1 | 9/2002 | Flaherty et al. |
| 2002/0128543 A1 | 9/2002 | Leonhardt |
| 2002/0147423 A1 | 10/2002 | Burbank et al. |

(56) References Cited

U.S. PATENT DOCUMENTS

| | | |
|---|---|---|
| 2002/0155425 A1 | 10/2002 | Han et al. |
| 2002/0161288 A1 | 10/2002 | Shin et al. |
| 2003/0023148 A1 | 1/2003 | Lorenz et al. |
| 2003/0050621 A1 | 3/2003 | Lebel et al. |
| 2003/0060692 A1 | 3/2003 | Ruchti et al. |
| 2003/0086074 A1 | 5/2003 | Braig et al. |
| 2003/0086075 A1 | 5/2003 | Braig et al. |
| 2003/0090649 A1 | 5/2003 | Sterling et al. |
| 2003/0100040 A1 | 5/2003 | Bonnecaze et al. |
| 2003/0130616 A1 | 7/2003 | Steil et al. |
| 2003/0135388 A1 | 7/2003 | Martucci et al. |
| 2003/0144582 A1 | 7/2003 | Cohen et al. |
| 2003/0163097 A1 | 8/2003 | Fleury et al. |
| 2003/0195404 A1 | 10/2003 | Knobbe et al. |
| 2003/0208113 A1 | 11/2003 | Mault et al. |
| 2003/0208154 A1 | 11/2003 | Close et al. |
| 2003/0212379 A1 | 11/2003 | Bylund et al. |
| 2003/0216627 A1 | 11/2003 | Lorenz et al. |
| 2003/0220605 A1 | 11/2003 | Bowman, Jr. et al. |
| 2004/0010207 A1 | 1/2004 | Flaherty et al. |
| 2004/0034295 A1 | 2/2004 | Salganicoff |
| 2004/0045879 A1 | 3/2004 | Shults et al. |
| 2004/0051368 A1 | 3/2004 | Caputo et al. |
| 2004/0064259 A1 | 4/2004 | Haaland et al. |
| 2004/0097796 A1 | 5/2004 | Berman et al. |
| 2004/0116847 A1 | 6/2004 | Wall |
| 2004/0122353 A1 | 6/2004 | Shahmirian et al. |
| 2004/0133166 A1 | 7/2004 | Moberg et al. |
| 2004/0147034 A1 | 7/2004 | Gore et al. |
| 2004/0171983 A1 | 9/2004 | Sparks et al. |
| 2004/0203357 A1 | 10/2004 | Nassimi |
| 2004/0204868 A1 | 10/2004 | Maynard et al. |
| 2004/0215492 A1 | 10/2004 | Choi |
| 2004/0220517 A1 | 11/2004 | Starkweather et al. |
| 2004/0241736 A1 | 12/2004 | Hendee et al. |
| 2004/0249308 A1 | 12/2004 | Forssell |
| 2005/0003470 A1 | 1/2005 | Nelson et al. |
| 2005/0020980 A1 | 1/2005 | Inoue et al. |
| 2005/0022274 A1 | 1/2005 | Campbell et al. |
| 2005/0033148 A1 | 2/2005 | Haueter et al. |
| 2005/0049179 A1 | 3/2005 | Davidson et al. |
| 2005/0065464 A1 | 3/2005 | Talbot et al. |
| 2005/0065465 A1 | 3/2005 | Lebel et al. |
| 2005/0075624 A1 | 4/2005 | Miesel |
| 2005/0105095 A1 | 5/2005 | Pesach et al. |
| 2005/0137573 A1 | 6/2005 | McLaughlin |
| 2005/0171503 A1 | 8/2005 | Van Den Berghe et al. |
| 2005/0182306 A1 | 8/2005 | Sloan |
| 2005/0192494 A1 | 9/2005 | Ginsberg |
| 2005/0192557 A1 | 9/2005 | Brauker et al. |
| 2005/0197621 A1 | 9/2005 | Poulsen et al. |
| 2005/0203360 A1 | 9/2005 | Brauker et al. |
| 2005/0203461 A1 | 9/2005 | Flaherty et al. |
| 2005/0238507 A1 | 10/2005 | Dilanni et al. |
| 2005/0261660 A1 | 11/2005 | Choi |
| 2005/0272640 A1 | 12/2005 | Doyle, III et al. |
| 2005/0277912 A1 | 12/2005 | John |
| 2006/0009727 A1 | 1/2006 | OMahony et al. |
| 2006/0079809 A1 | 4/2006 | Goldberger et al. |
| 2006/0100494 A1 | 5/2006 | Kroll |
| 2006/0134323 A1 | 6/2006 | OBrien |
| 2006/0167350 A1 | 7/2006 | Monfre et al. |
| 2006/0173406 A1 | 8/2006 | Hayes et al. |
| 2006/0189925 A1 | 8/2006 | Gable et al. |
| 2006/0189926 A1 | 8/2006 | Hall et al. |
| 2006/0197015 A1 | 9/2006 | Sterling et al. |
| 2006/0200070 A1 | 9/2006 | Callicoat et al. |
| 2006/0204535 A1 | 9/2006 | Johnson |
| 2006/0229531 A1 | 10/2006 | Goldberger et al. |
| 2006/0253085 A1 | 11/2006 | Geismar et al. |
| 2006/0264895 A1 | 11/2006 | Flanders |
| 2006/0270983 A1 | 11/2006 | Lord et al. |
| 2006/0276771 A1 | 12/2006 | Galley et al. |
| 2006/0282290 A1 | 12/2006 | Flaherty et al. |
| 2007/0016127 A1 | 1/2007 | Staib et al. |
| 2007/0060796 A1 | 3/2007 | Kim |
| 2007/0060869 A1 | 3/2007 | Tolle et al. |
| 2007/0060872 A1 | 3/2007 | Hall et al. |
| 2007/0083160 A1 | 4/2007 | Hall et al. |
| 2007/0106135 A1 | 5/2007 | Sloan et al. |
| 2007/0116601 A1 | 5/2007 | Patton |
| 2007/0118405 A1 | 5/2007 | Campbell et al. |
| 2007/0129690 A1 | 6/2007 | Rosenblatt et al. |
| 2007/0142720 A1 | 6/2007 | Ridder et al. |
| 2007/0173761 A1 | 7/2007 | Kanderian et al. |
| 2007/0173974 A1 | 7/2007 | Lin |
| 2007/0179352 A1 | 8/2007 | Randlov et al. |
| 2007/0191716 A1 | 8/2007 | Goldberger et al. |
| 2007/0197163 A1 | 8/2007 | Robertson |
| 2007/0225675 A1 | 9/2007 | Robinson et al. |
| 2007/0244381 A1 | 10/2007 | Robinson et al. |
| 2007/0249007 A1 | 10/2007 | Rosero |
| 2007/0264707 A1 | 11/2007 | Liederman et al. |
| 2007/0282269 A1 | 12/2007 | Carter et al. |
| 2007/0287985 A1 | 12/2007 | Estes et al. |
| 2007/0293843 A1 | 12/2007 | Ireland et al. |
| 2008/0033272 A1 | 2/2008 | Gough et al. |
| 2008/0051764 A1 | 2/2008 | Dent et al. |
| 2008/0058625 A1 | 3/2008 | McGarraugh et al. |
| 2008/0065050 A1 | 3/2008 | Sparks et al. |
| 2008/0071157 A1 | 3/2008 | McGarraugh et al. |
| 2008/0071158 A1 | 3/2008 | McGarraugh et al. |
| 2008/0078400 A1 | 4/2008 | Martens et al. |
| 2008/0097289 A1 | 4/2008 | Steil et al. |
| 2008/0132880 A1 | 6/2008 | Buchman |
| 2008/0161664 A1 | 7/2008 | Mastrototaro et al. |
| 2008/0172026 A1 | 7/2008 | Blomquist |
| 2008/0177165 A1 | 7/2008 | Blomquist et al. |
| 2008/0188796 A1 | 8/2008 | Steil et al. |
| 2008/0200838 A1 | 8/2008 | Goldberger et al. |
| 2008/0206067 A1 | 8/2008 | De Corral et al. |
| 2008/0208113 A1 | 8/2008 | Damiano et al. |
| 2008/0214919 A1 | 9/2008 | Harmon et al. |
| 2008/0228056 A1 | 9/2008 | Blomquist et al. |
| 2008/0249386 A1 | 10/2008 | Besterman et al. |
| 2008/0269585 A1 | 10/2008 | Ginsberg |
| 2008/0269714 A1 | 10/2008 | Mastrototaro et al. |
| 2008/0269723 A1 | 10/2008 | Mastrototaro et al. |
| 2008/0287906 A1 | 11/2008 | Burkholz et al. |
| 2009/0006061 A1 | 1/2009 | Thukral et al. |
| 2009/0018406 A1 | 1/2009 | Yodfat et al. |
| 2009/0030398 A1 | 1/2009 | Yodfat et al. |
| 2009/0036753 A1 | 2/2009 | King |
| 2009/0043240 A1 | 2/2009 | Robinson et al. |
| 2009/0054753 A1 | 2/2009 | Robinson et al. |
| 2009/0069743 A1 | 3/2009 | Krishnamoorthy et al. |
| 2009/0069745 A1 | 3/2009 | Estes et al. |
| 2009/0069787 A1 | 3/2009 | Estes et al. |
| 2009/0099521 A1 | 4/2009 | Gravesen et al. |
| 2009/0105573 A1 | 4/2009 | Malecha |
| 2009/0105636 A1* | 4/2009 | Hayter .......... G16H 40/63 604/66 |
| 2009/0131861 A1 | 5/2009 | Braig et al. |
| 2009/0156922 A1 | 6/2009 | Goldberger et al. |
| 2009/0156924 A1 | 6/2009 | Shariati et al. |
| 2009/0163781 A1 | 6/2009 | Say et al. |
| 2009/0198350 A1 | 8/2009 | Thiele |
| 2009/0221890 A1 | 9/2009 | Saffer et al. |
| 2009/0228214 A1 | 9/2009 | Say et al. |
| 2009/0318791 A1 | 12/2009 | Kaastrup |
| 2009/0326343 A1 | 12/2009 | Gable et al. |
| 2010/0057042 A1 | 3/2010 | Hayter |
| 2010/0114026 A1 | 5/2010 | Karratt et al. |
| 2010/0121170 A1 | 5/2010 | Rule |
| 2010/0137784 A1 | 6/2010 | Cefai et al. |
| 2010/0152658 A1 | 6/2010 | Hanson et al. |
| 2010/0174228 A1 | 7/2010 | Buckingham et al. |
| 2010/0211003 A1 | 8/2010 | Sundar et al. |
| 2010/0228110 A1 | 9/2010 | Tsoukalis |
| 2010/0262117 A1 | 10/2010 | Magni et al. |
| 2010/0262434 A1 | 10/2010 | Shaya |
| 2010/0295686 A1 | 11/2010 | Sloan et al. |
| 2010/0298765 A1 | 11/2010 | Budiman et al. |
| 2011/0021584 A1 | 1/2011 | Berggren et al. |

(56) References Cited

U.S. PATENT DOCUMENTS

| | | |
|---|---|---|
| 2011/0028817 A1 | 2/2011 | Jin et al. |
| 2011/0054390 A1 | 3/2011 | Searle et al. |
| 2011/0054399 A1 | 3/2011 | Chong et al. |
| 2011/0124996 A1 | 5/2011 | Reinke et al. |
| 2011/0144586 A1 | 6/2011 | Michaud et al. |
| 2011/0160652 A1 | 6/2011 | Yodfat et al. |
| 2011/0178472 A1 | 7/2011 | Cabiri |
| 2011/0190694 A1 | 8/2011 | Lanier, Jr. et al. |
| 2011/0202005 A1 | 8/2011 | Yodfat et al. |
| 2011/0218495 A1 | 9/2011 | Remde |
| 2011/0230833 A1 | 9/2011 | Landman et al. |
| 2011/0251509 A1 | 10/2011 | Beyhan et al. |
| 2011/0313680 A1 | 12/2011 | Doyle et al. |
| 2011/0316562 A1 | 12/2011 | Cefai et al. |
| 2012/0003935 A1 | 1/2012 | Lydon et al. |
| 2012/0010594 A1 | 1/2012 | Holt et al. |
| 2012/0030393 A1 | 2/2012 | Ganesh et al. |
| 2012/0053556 A1 | 3/2012 | Lee |
| 2012/0078067 A1 | 3/2012 | Kovatchev et al. |
| 2012/0078161 A1 | 3/2012 | Masterson et al. |
| 2012/0078181 A1 | 3/2012 | Smith et al. |
| 2012/0101451 A1 | 4/2012 | Boit et al. |
| 2012/0123234 A1 | 5/2012 | Atlas et al. |
| 2012/0136336 A1 | 5/2012 | Mastrototaro et al. |
| 2012/0190955 A1 | 7/2012 | Rao et al. |
| 2012/0203085 A1 | 8/2012 | Rebec |
| 2012/0203178 A1 | 8/2012 | Tverskoy |
| 2012/0215087 A1 | 8/2012 | Cobelli et al. |
| 2012/0225134 A1 | 9/2012 | Komorowski |
| 2012/0226259 A1 | 9/2012 | Yodfat et al. |
| 2012/0232520 A1 | 9/2012 | Sloan et al. |
| 2012/0238851 A1 | 9/2012 | Kamen et al. |
| 2012/0271655 A1 | 10/2012 | Knobel et al. |
| 2012/0277668 A1 | 11/2012 | Chawla |
| 2012/0282111 A1 | 11/2012 | Nip et al. |
| 2012/0295550 A1 | 11/2012 | Wilson et al. |
| 2013/0030358 A1 | 1/2013 | Yodfat et al. |
| 2013/0158503 A1 | 6/2013 | Kanderian, Jr. et al. |
| 2013/0178791 A1 | 7/2013 | Javitt |
| 2013/0231642 A1 | 9/2013 | Doyle et al. |
| 2013/0253472 A1 | 9/2013 | Cabiri |
| 2013/0261406 A1 | 10/2013 | Rebec et al. |
| 2013/0296823 A1 | 11/2013 | Melker et al. |
| 2013/0317753 A1 | 11/2013 | Kamen et al. |
| 2013/0338576 A1 | 12/2013 | OConnor et al. |
| 2014/0005633 A1 | 1/2014 | Finan |
| 2014/0066886 A1 | 3/2014 | Roy et al. |
| 2014/0074033 A1 | 3/2014 | Sonderegger et al. |
| 2014/0121635 A1 | 5/2014 | Hayter |
| 2014/0128839 A1 | 5/2014 | Dilanni et al. |
| 2014/0135880 A1 | 5/2014 | Baumgartner et al. |
| 2014/0146202 A1 | 5/2014 | Boss et al. |
| 2014/0180203 A1 | 6/2014 | Budiman et al. |
| 2014/0180240 A1 | 6/2014 | Finan et al. |
| 2014/0200426 A1 | 7/2014 | Taub et al. |
| 2014/0200559 A1 | 7/2014 | Doyle et al. |
| 2014/0230021 A1 | 8/2014 | Birtwhistle et al. |
| 2014/0276554 A1 | 9/2014 | Finan et al. |
| 2014/0276556 A1 | 9/2014 | Saint et al. |
| 2014/0278123 A1 | 9/2014 | Prodhom et al. |
| 2014/0309615 A1 | 10/2014 | Mazlish |
| 2014/0316379 A1 | 10/2014 | Sonderegger et al. |
| 2014/0325065 A1 | 10/2014 | Birtwhistle et al. |
| 2015/0018633 A1 | 1/2015 | Kovachev et al. |
| 2015/0025329 A1 | 1/2015 | Amarasingham et al. |
| 2015/0025495 A1 | 1/2015 | Peyser |
| 2015/0120317 A1 | 4/2015 | Mayou et al. |
| 2015/0134265 A1 | 5/2015 | Kohlbrecher et al. |
| 2015/0165119 A1 | 6/2015 | Palerm et al. |
| 2015/0173674 A1 | 6/2015 | Hayes et al. |
| 2015/0213217 A1 | 7/2015 | Amarasingham et al. |
| 2015/0217052 A1 | 8/2015 | Keenan et al. |
| 2015/0217053 A1 | 8/2015 | Booth et al. |
| 2015/0265767 A1 | 9/2015 | Vazquez et al. |
| 2015/0306314 A1 | 10/2015 | Doyle et al. |
| 2015/0351671 A1 | 12/2015 | Vanslyke et al. |
| 2015/0366945 A1 | 12/2015 | Greene |
| 2016/0015891 A1 | 1/2016 | Papiorek |
| 2016/0038673 A1 | 2/2016 | Morales |
| 2016/0038689 A1 | 2/2016 | Lee et al. |
| 2016/0051749 A1 | 2/2016 | Istoc |
| 2016/0082187 A1 | 3/2016 | Schaible et al. |
| 2016/0089494 A1 | 3/2016 | Guerrini |
| 2016/0175520 A1 | 6/2016 | Palerm et al. |
| 2016/0228641 A1 | 8/2016 | Gescheit et al. |
| 2016/0243318 A1 | 8/2016 | Despa et al. |
| 2016/0256087 A1 | 9/2016 | Doyle et al. |
| 2016/0287512 A1 | 10/2016 | Cooper et al. |
| 2016/0302054 A1 | 10/2016 | Kimura et al. |
| 2016/0331310 A1 | 11/2016 | Kovatchev |
| 2016/0354543 A1 | 12/2016 | Cinar et al. |
| 2017/0049386 A1 | 2/2017 | Abraham et al. |
| 2017/0143899 A1 | 5/2017 | Gondhalekar et al. |
| 2017/0143900 A1 | 5/2017 | Rioux et al. |
| 2017/0156682 A1 | 6/2017 | Doyle et al. |
| 2017/0173261 A1 | 6/2017 | OConnor et al. |
| 2017/0189625 A1 | 7/2017 | Cirillo et al. |
| 2017/0281877 A1 | 10/2017 | Marlin et al. |
| 2017/0296746 A1 | 10/2017 | Chen et al. |
| 2017/0311903 A1 | 11/2017 | Davis et al. |
| 2017/0348482 A1 | 12/2017 | Duke et al. |
| 2018/0036495 A1 | 2/2018 | Searle et al. |
| 2018/0040255 A1 | 2/2018 | Freeman et al. |
| 2018/0075200 A1 | 3/2018 | Davis et al. |
| 2018/0075201 A1 | 3/2018 | Davis et al. |
| 2018/0075202 A1 | 3/2018 | Davis et al. |
| 2018/0092576 A1 | 4/2018 | Ambrosio |
| 2018/0126073 A1* | 5/2018 | Wu .............. G16H 40/63 |
| 2018/0169334 A1 | 6/2018 | Grosman et al. |
| 2018/0200434 A1 | 7/2018 | Mazlish et al. |
| 2018/0200438 A1 | 7/2018 | Mazlish et al. |
| 2018/0200441 A1 | 7/2018 | Desborough et al. |
| 2018/0204636 A1 | 7/2018 | Edwards et al. |
| 2018/0277253 A1 | 9/2018 | Gondhalekar et al. |
| 2018/0289891 A1 | 10/2018 | Finan et al. |
| 2018/0296757 A1 | 10/2018 | Finan et al. |
| 2018/0342317 A1 | 11/2018 | Skirble et al. |
| 2018/0369479 A1 | 12/2018 | Hayter et al. |
| 2019/0076600 A1 | 3/2019 | Grosman et al. |
| 2019/0240403 A1* | 8/2019 | Palerm .............. A61B 5/4839 |
| 2019/0290844 A1 | 9/2019 | Monirabbasi et al. |
| 2019/0336683 A1 | 11/2019 | OConnor et al. |
| 2019/0336684 A1 | 11/2019 | OConnor et al. |
| 2019/0348157 A1 | 11/2019 | Booth et al. |
| 2020/0046268 A1 | 2/2020 | Patek et al. |
| 2020/0101222 A1 | 4/2020 | Lintereur et al. |
| 2020/0101223 A1 | 4/2020 | Lintereur et al. |
| 2020/0101225 A1 | 4/2020 | OConnor et al. |
| 2020/0219625 A1 | 7/2020 | Kahlbaugh |
| 2020/0342974 A1 | 10/2020 | Chen et al. |
| 2021/0050085 A1 | 2/2021 | Hayter et al. |
| 2021/0098105 A1 | 4/2021 | Lee et al. |
| 2022/0023536 A1 | 1/2022 | Graham et al. |

FOREIGN PATENT DOCUMENTS

| | | |
|---|---|---|
| CN | 1297140 A | 5/2001 |
| DE | 19756872 A1 | 7/1999 |
| EP | 0341049 A2 | 11/1989 |
| EP | 0496305 A2 | 7/1992 |
| EP | 0549341 A1 | 6/1993 |
| EP | 1491144 A1 | 12/2004 |
| EP | 1571582 A2 | 9/2005 |
| EP | 0801578 B1 | 7/2006 |
| EP | 2666520 A1 | 10/2009 |
| EP | 2139382 A1 | 1/2010 |
| EP | 2397181 A1 | 12/2011 |
| EP | 2695573 A2 | 2/2014 |
| EP | 2830499 A1 | 2/2015 |
| EP | 2943149 A1 | 11/2015 |
| EP | 3177344 A1 | 6/2017 |
| EP | 3314548 A1 | 5/2018 |
| EP | 2897071 B1 | 5/2019 |
| EP | 3607985 A1 | 2/2020 |

(56) References Cited

FOREIGN PATENT DOCUMENTS

| | | |
|---|---|---|
| GB | 2443261 A | 4/2008 |
| JP | 51125993 A | 11/1976 |
| JP | 02131777 A | 5/1990 |
| JP | 2004283378 A | 10/2004 |
| JP | 2017525451 A | 9/2017 |
| JP | 2018153569 A | 10/2018 |
| JP | 2019525276 A | 9/2019 |
| TW | 200740148 A | 10/2007 |
| TW | M452390 U | 5/2013 |
| WO | 9800193 A1 | 1/1998 |
| WO | 9956803 A1 | 11/1999 |
| WO | 0030705 A1 | 6/2000 |
| WO | 0032258 A1 | 6/2000 |
| WO | 0172354 A2 | 10/2001 |
| WO | 2002015954 A1 | 2/2002 |
| WO | 0243866 A2 | 6/2002 |
| WO | 02082990 A1 | 10/2002 |
| WO | 03016882 A1 | 2/2003 |
| WO | 03039362 A1 | 5/2003 |
| WO | 03045233 A1 | 6/2003 |
| WO | 2004043250 A1 | 5/2004 |
| WO | 2004092715 A1 | 10/2004 |
| WO | 2005051170 A2 | 6/2005 |
| WO | 2005082436 A1 | 9/2005 |
| WO | 05110601 A1 | 11/2005 |
| WO | 2005113036 A1 | 12/2005 |
| WO | 2006053007 A2 | 5/2006 |
| WO | 2007064835 A2 | 6/2007 |
| WO | 2007078937 A1 | 7/2007 |
| WO | 2008024810 A2 | 2/2008 |
| WO | 2008029403 A1 | 3/2008 |
| WO | 2008133702 A1 | 11/2008 |
| WO | 2009045462 A1 | 4/2009 |
| WO | 2009049252 A1 | 4/2009 |
| WO | 2009066287 A3 | 5/2009 |
| WO | 2009066288 A1 | 5/2009 |
| WO | 2009098648 A2 | 8/2009 |
| WO | 2009134380 A2 | 11/2009 |
| WO | 2010053702 A1 | 5/2010 |
| WO | 2010132077 A1 | 11/2010 |
| WO | 2010138848 A1 | 12/2010 |
| WO | 2010147659 A2 | 12/2010 |
| WO | 2011095483 A1 | 8/2011 |
| WO | 2012045667 A2 | 4/2012 |
| WO | 2012108959 A1 | 8/2012 |
| WO | 2012134588 A1 | 10/2012 |
| WO | 2012177353 A1 | 12/2012 |
| WO | 2012178134 A2 | 12/2012 |
| WO | 2013078200 A1 | 5/2013 |
| WO | 2013134486 A2 | 9/2013 |
| WO | 20130149186 A1 | 10/2013 |
| WO | 2013177565 A1 | 11/2013 |
| WO | 2013182321 A1 | 12/2013 |
| WO | 2014109898 A1 | 7/2014 |
| WO | 2014110538 A1 | 7/2014 |
| WO | 2014194183 A2 | 12/2014 |
| WO | 2015056259 A1 | 4/2015 |
| WO | 2015061493 A1 | 4/2015 |
| WO | 2015073211 A1 | 5/2015 |
| WO | 2015081337 A2 | 6/2015 |
| WO | 2015187366 A1 | 12/2015 |
| WO | 2016004088 A1 | 1/2016 |
| WO | 2016022650 A1 | 2/2016 |
| WO | 2016041873 A1 | 3/2016 |
| WO | 2016089702 A1 | 6/2016 |
| WO | 2016141082 A1 | 9/2016 |
| WO | 2016161254 A1 | 10/2016 |
| WO | 2017004278 A1 | 1/2017 |
| WO | 2017091624 A1 | 6/2017 |
| WO | 2017105600 A1 | 6/2017 |
| WO | 2017184988 A1 | 10/2017 |
| WO | 2017205816 A1 | 11/2017 |
| WO | 2018009614 A1 | 1/2018 |
| WO | 2018067748 A1 | 4/2018 |
| WO | 2018120104 A1 | 7/2018 |
| WO | 2018136799 A1 | 7/2018 |
| WO | 2018204568 A1 | 11/2018 |
| WO | 2019077482 A1 | 4/2019 |
| WO | 2019094440 A1 | 5/2019 |
| WO | 2019213493 A1 | 11/2019 |
| WO | 2019246381 A1 | 12/2019 |
| WO | 2020081393 A1 | 4/2020 |
| WO | 2021011738 A1 | 1/2021 |

OTHER PUBLICATIONS

International Search Report and Written Opinion for the International Patent Application No. PCT/US2020/052125, dated Aug. 12, 2020, 15 pages.

International Search Report and Written Opinion for the International Patent Application No. PCT/US2020/050332, dated Sep. 12, 2020, 12 pages.

European Patent Office, "Notification of Transmittal of the ISR and the Written Opinion of the International Searching Authority, or the Declaration," in PCT Application No. PCT/GB2015/050248, dated Jun. 23, 2015, 12 pages.

International Search Report and Written Opinion for International Patent Application No. PCT/US2021/051027, dated Jan. 7, 2022, 16 pages.

International Search Report and Written Opinion for International Patent Application No. PCT/US2021/052372, dated Jan. 26, 2022, 15 pages.

International Search Report and Written Opinion for the International Patent Application No. PCT/US2021/046607, dated Jan. 31, 2022, 20 pages.

International Search Report and Written Opinion for the International Patent Application No. PCT/US2021/055745, dated Feb. 14, 2022, 13 pages.

Anonymous: "Artificial pancreas—Wikipedia", Mar. 13, 2018 (Mar. 13, 2018), XP055603712, Retrieved from the Internet: URL: https://en.wikipedia.org/wiki/Artificial_pancreas [retrieved on Jul. 9, 2019] section "Medical Equipment" and the figure labeled "The medical equipment approach to an artifical pancreas".

Kaveh et al., "Blood Glucose Regulation via Double Loop Higher Order Sliding Mode Control and Multiple Sampling Rate." Paper presented at the proceedings of the 17th IFAC World Congress, Seoul, Korea (Jul. 2008).

Dassau et al., "Real-Time Hypoglycemia Prediction Suite Using Contineous Glucose Monitoring," Diabetes Care, vol. 33, No. 6, 1249-1254 (2010).

International Search Report and Written Opinion for International Patent Application No. PCT/US17/53262, dated Dec. 13, 2017, 8 pages.

Van Heusden et al., "Control-Relevant Models for Glucose Control using a Priori Patient Characteristics", IEEE Transactions on Biomedical Engineering, vol. 59, No. 7, (Jul. 1, 2012) pp. 1839-1849.

Doyle III et al., "Run-to-Run Control Strategy for Diabetes Management." Paper presented at 23rd Annual International Conference of the IEEE Engineering in Medicine and Biology Society, Istanbul, Turkey. (Jul. 2001).

Bequette, B.W., and Desemone, J., "Intelligent Dosing Systems": Need for Design and Analysis Based on Control Theory, Diabetes Technology and Therapeutics 9(6): 868-873 (2004).

Parker et al., "A Model-Based Agorithm for Blood Gucose Control in Type 1 Diabetic Patients." IEEE Transactions on Biomedical Engineering, 46 (2) 148-147 (1999).

International Search Report and Written Opinion for International Patent Application No. PCT/US2017/015601, dated May 16, 2017, 12 pages.

International Search Report and Written Opinion for the International Patent Application No. PCT/US2018/018901, dated Aug. 6, 2018, 12 pages.

International Search Report and Written Opinion for International Patent Application No. PCT/US2018/052467, dated Jan. 4, 2019, 13 pages.

"How to Create a QR Code that Deep Links to Your Mobile App", Pure Oxygen Labs, web<https://pureoxygenlabs.com/how-to-create-a-qr-codes-that-deep-link-to-your-mobile-app/>. Year:2017.

(56) References Cited

OTHER PUBLICATIONS

"Read NFC Tags with an iPHone App on IOS 11", GoToTags, Sep. 11, 2017, web <https://gototags.com/blog/read-nfc-tags-with-an-iphone-app-on-ios-11/>. (Year:2017).
International Search Report and Written Opinion for International Patent Application No. PCT/US2016/063350, dated Mar. 27, 2017, 9 pages.
Extended Search Report dated Aug. 13, 2018, issued in European Patent Application No. 16753053.4, 9 pages.
International Search Report and Written Opinion for International Patent Application No. PCT/US16/18452, dated Apr. 29, 2015, 9 pages.
International Preliminary Report on Patentability dated Aug. 31, 2017, issued in PCT Patent Application No. PCT/US2016/018452, 7 pages.
International Search Report and Written Opinion for International Patent Application No. PCT/US2019/055862, dated Mar. 11, 2020.
Kohdaei et al., "Physiological Closed-Loop Contol (PCLC) Systems: Review of a Modern Frontier in Automation", IEEE Access, IEEE, USA, vol. 8, Jan. 20, 2020, pp. 23965-24005.
E. Atlas et al., "MD-Logic Artificial Pancreas System: A pilot study in adults with type 1 diabetes", Diabetes Care, vol. 33, No. 5, Feb. 11, 2010, pp. 1071-1076.
Anonymous: "Fuzzy control system", Wikipedia, Jan. 10, 2020. URL: https://en.wikipedia.org/w/index.php?title=Fuzzy_control_system&oldid=935091190.
European Search Report for the European Patent Application No. 21168591.2, dated Oct. 13, 2021, 151 pages.
International Search Report and Written Opinion for the International Patent Application No. PCT/US2021/041954, dated Oct. 25, 2021, 13 pages.
International Search Report and Written Opinion for the International Patent Application No. PCT/US2021/047771, dated Dec. 22, 2021, 11 pages.
International Search Report and Written Opinion for the International Patent Application No. PCT/US2021/052855, dated Dec. 22, 2021, 11 pages.
Unger, Jeff, et al., "Glucose Control in the Hospitalized Patient," Emerg. Med 36(9):12-18 (2004).
Glucommander FAQ downloaded from https://adaendo.com/GlucommanderFAQ.html on Mar. 16, 2009.
Finfer, Simon & Heritier, Stephane. (2009). The NICE-SUGAR (Normoglycaemia in Intensive Care Evaluation and Survival Using Glucose Algorithm Regulation) Study: statistical analysis plan. Critical care and resuscitation : journal of the Australasian Academy of Critical Care Medicine. 11. 46-57.
Letters to the Editor regarding "Glucose Control in Critically Ill Patients," N Engl J Med 361: 1, Jul. 2, 2009.
"Medtronic is Leading a Highly Attractive Growth Market," Jun. 2, 2009.
Davidson, Paul C., et al. "Glucommander: An Adaptive, Computer-Directed System for IV Insulin Shown to be Safe, Simple, and Effective in 120,618 Hours of Operation," Atlanta Diabetes Associates presentation Nov. 16, 2003.
Davidson, Paul C., et al. "Pumpmaster and Glucommander," presented at the MiniMed Symposium, Atlanta GA, Dec. 13, 2003.
Kanji S., et al. "Reliability of point-of-care testing for glucose measurement in critically ill adults," Critical Care Med, vol. 33, No. 12, pp. 2778-2785, 2005.
Krinsley James S., "Severe hypoglycemia in critically ill patients: Risk factors and outcomes," Critical Care Med, vol. 35, No. 10, pp. 1-6, 2007.
International Searching Authority, Invitation to Pay Additional Fees, International Application No. PCT/US2006/004929, dated Jul. 27, 2006.
Farkas et al. "Single-Versus Triple-Lumen Central Catheter-Related Sepsis: A Prospective Randomized Study in a Critically Ill Population" The American Journal of Medicine Sep. 1992 vol. 93 p. 277-282.
Davidson, Paul C., et al., A computer-directed intravenous insulin system shown to be safe, simple, and effective in 120,618 h of operation, Diabetes Care, vol. 28, No. 10, Oct. 2005, pp. 2418-2423.
International Search Report and Written Opinion for the International Patent Application No. PCT/US2021/016283, dated Jun. 2, 2021, 15 pages.
Gorke, A. "Microbial contamination of haemodialysis catheter connections." EDTNA/ERCA journal (English ed.) vol. 31,2 (2005): 79-84. doi:10.1111/j.1755-6686.2005.tb00399.x.
Lovich et al. "Central venous catheter infusions: A laboratory model shows large differences in drug delivery dynamics related to catheter dead volume" Critical Care Med 2007 vol. 35, No. 12.
Van Den Berghe, Greet, M.D., Ph.D., et al., Intensive Insulin Therapy in Critically Ill Patients, The New England Journal of Medicine, vol. 345, No. 19, Nov. 8, 2001, pp. 1359-1367.
Templeton et al., "Multilumen Central Venous Catheters Increase Risk for Catheter-Related Bloodstream Infection: Prospective Surveillance Study" Infection 2008; 36: 322-327.
Wilson, George S., et al., Progress toward the Development of an Implantable Sensor for Glucose, Clin. Chem., vol. 38, No. 9, 1992, pp. 1613-1617.
Yeung et al. "Infection Rate for Single Lumen v Triple Lumen Subclavian Catheters" Infection Control and Hospital Epidemiology, vol. 9, No. 4 (Apr. 1988) pp. 154-158 The University of Chicago Press.
International Search Report and Written Opinion, International Application No. PCT/US2010/033794 dated Jul. 16, 2010.
International Search Report and Written Opinion in PCT/US2008/079641 dated Feb. 25, 2009.
Berger, "Measurement of Analytes in Human Serum and Whole Blood Samples by Near-Infrared Raman Spectroscopy," Ph.D. Thesis, Massachusetts Institute of Technology, Chapter 4, pp. 50-73, 1998.
Berger, "An Enhanced Algorithm for Linear Multivariate Calibration," Analytical Chemistry, vol. 70, No. 3, pp. 623-627, Feb. 1, 1998.
Billman et al., "Clinical Performance of an in line Ex-Vivo Point of Care Monitor: A Multicenter Study," Clinical Chemistry 48: 11, pp. 2030-2043, 2002.
Widness et al., "Clinical Performance on an In-Line Point-of-Care Monitor in Neonates"; Pediatrics, vol. 106, No. 3, pp. 497-504, Sep. 2000.
Finkielman et al., "Agreement Between Bedside Blood and Plasma Glucose Measurement in the ICU Setting"; retrieved from http://www.chestjournal.org; CHEST/127/5/May 2005.
Glucon Critical Care Blood Glucose Monitor; Glucon; retrieved from http://www.glucon.com.
Fogt, et al., "Development and Evaluation of a Glucose Analyzer for a Glucose-Controlled Insulin Infusion System (Biostator)"; Clinical Chemistry, vol. 24, No. 8, pp. 1366-1372, 1978.
Vonach et al., "Application of Mid-Infrared Transmission Spectrometry to the Direct Determination of Glucose in Whole Blood, " Applied Spectroscopy, vol. 52, No. 6, 1998, pp. 820-822.
Muniyappa et al., "Current Approaches for assessing insulin sensitivity and resistance in vivo: advantages, imitations, and appropriate usage," AJP-Endocrinol Metab, vol. 294, E15-E26, first published Oct. 23, 2007.
R Anthony Shaw, et al., "Infrared Spectroscopy in Clinical and Dianostic Analysis," Encyclopedia of Analytical Chemistry, ed. Robert A. Meyers, John Wiley & Sons, Ltd., pp. 1-20, 2000.
International Preliminary Report on Patentability for the International Patent Application No. PCT/US2019/053603, dated Apr. 8, 2021, 9 pages.
International Search Report and Written Opinion for the International Patent Application No. PCT/US2019/053603, dated Jan. 7, 2020, 16 pages.
Dassau et al., "Detection of a meal using continuous glucose monitoring: Implications for an artificial [beta]-cell." Diabetes Care, American Diabetes Association, Alexandria, VA, US, 31(2):295-300 (2008).

(56) References Cited

OTHER PUBLICATIONS

Cameron et al., "Probabilistic Evolving Meal Detection and Estimation of Meal Total Glucose Appearance Author Affiliations", J Diabetes Sci and Tech, vol. Diabetes Technology Society ;(5):1022-1030 (2009).

Lee et al., "A closed-loop artificial pancreas based on model predictive control: Human-friendly identification and automatic meal disturbance rejection", Biomedical Signal Processing and Control, Elsevier, Amsterdam, NL, 4(4):1746-8094 (2009).

International Search Report and Written Opinion for the InternationalPatent Application No. PCT/US2021/018297, dated May 18, 2021, 18 pages.

An Emilia Fushimi: "Artificial Pancreas: Evaluating the ARG Algorithm Without Meal Announcement", Journal of Diabetes Science and Technology Diabetes Technology Society, Mar. 22, 2019, pp. 1025-1043.

International Search Report and Written Opinion for the International Patent Application No. PCT/US2021/017441, dated May 25, 2021, 12 pages.

International Search Report and Written Opinion for the InternationalPatent Application No. PCT/US2021/017664, dated May 26, 2021, 16 pages.

Mirko Messori et al: "Individualized model predictive control for the artificial pancreas: In silico evaluation of closed-loop glucose control", IEEE Control Systems, vol. 38, No. 1, Feb. 1, 2018, pp. 86-104.

International Search Report and Written Opinion for the International Patent Application No. PCT/US2021/017662, dated May 26, 2021, 14 pages.

Anonymous: "Reservoir Best Practice and Top Tips" Feb. 7, 2016, URL: https://www.medtronic-diabetes.co.uk/blog/reservoir-best-practice-and-top-tips, p. 1.

Gildon Bradford: "InPen Smart Insulin Pen System: Product Review and User Experience" Diabetes Spectrum, vol. 31, No. 4, Nov. 15, 2018, pp. 354-358.

International Search Report and Written Opinion for the International Patent Application No. PCT/US2021/016050, dated May 27, 2021, 16 pages.

International Search Report and Written Opinion for the International Patent Application No. PCT/US2020/065226, dated May 31, 2021, 18 pages.

International Search Report and Written Opinion for the International Patent Application No. PCT/US2021/017659, dated May 31, 2021, 13 pages.

Montaser Eslam et al., "Seasonal Local Models for Glucose Prediction in Type 1 Diabetes", IEE Journal of Biomedical and Health Informatics, IEEE, Piscataway, NJ, USA, vol. 24, No. 7, Nov. 29, 2019, pp. 2064-2072.

Samadi Sediqeh et al., "Automatic Detection and Estimation of Unannouced Meals for Multivariable Artificial Pancreas System", Diabetis Technology & Therapeutics, vol. 20m No. 3, Mar. 1, 2018, pp. 235-246.

Samadi Sediqeh et al., "Meal Detection and Carbohydrate Estimation Using Continuous Glucose Sensor Data" IEEE Journal of Biomedical and Health Informatics, IEEE, Piscataway, NJ, USA, vol. 21, No. 3, May 1, 2017, pp. 619-627.

Montaser Eslam et al., "Seasonal Local Models for Glucose Prediction in Type 1 Diabetes", IEE Journal of Biomedical and Health Informatics, IEEE, Piscataway, NJ, USA, vol. 24, No. 7, Jul. 2020, pp. 2064-2072.

Khodaei et al., "Physiological Closed-Loop Contol (PCLC) Systems: Review of a Modern Frontier in Automation", IEEE Access, IEEE, USA, vol. 8, Jan. 20, 2020, pp. 23965-24005.

Anonymous: "Fuzzy control system", Wikipedia, Jan. 10, 2020. URL: https://en.wikipedia.org/w/index.php?title=Fuzzy_control_system&oldid=935091190 Retrieved: May 25, 2021.

International Search Report and Written Opinion for the International Patent Application No. PCT/US2021/022694, dated Jun. 25, 2021, 13 pages.

International Search Report and Written Opinion for the International Patent Application No. PCT/US2022/013470, dated May 6, 2022, 14 pages.

International Search Report and Written Opinion for the International Patent Application No. PCT/US2022/013473, dated May 6, 2022, 13 pages.

International Search Report and Written Opinion for the International Patent Application No. PCT/US2022/019079, dated Jun. 2, 2022, 14 pages.

International Search Report and Written Opinion for the International Patent Application No. PCT/US2022/018453, dated Jun. 2, 2022, 13 pages.

International Search Report and Written Opinion for the International Patent Application No. PCT/US22/018700, dated Jun. 7, 2022, 13 pages.

International Search Report and Written Opinion for the International Patent Application No. PCT/US22/019080, dated Jun. 7, 2022, 14 pages.

International Search Report and Written Opinion for the International Patent Application No. PCT/US22/019664, dated Jun. 7, 2022, 14 pages.

International Search Report and Written Opinion for the International Patent Application No. PCT/US21/060618, dated Mar. 21, 2022, 15 pages.

Herrero Pau et al: "Enhancing automatic closed-loop glucose control in type 1 diabetes with an adaptive meal bolus calculator -in silicoevaluation under intra-day variability", Computer Methods and Programs in Biomedicine, Elsevier, Amsterdam, NL, vol. 146, Jun. 1, 2017 (Jun. 1, 2017), pp. 125-131, XP085115607, ISSN: 0169-2607, DOI:10.1016/J.CMPB.2017.05.010.

Marie Aude Qemerais: "Preliminary Evaluation of a New Semi-Closed-Loop Insulin Therapy System over the prandial beriod in Adult Patients with type I diabetes: the WP6. 0 Diabeloop Study", Journal of Diabetes Science and Technology Diabetes Technology Society Reprints and permissions, Jan. 1, 2014, pp. 1177-1184, Retrieved from the Internet: URL:http://journals.sagepub.com/doi/pdf/10.1177/1932296814545668 [retrieved on Jun. 6, 2022] chapter "Functioning of the Algorithm" chapter "Statistical Analysis" p. 1183, left-hand column, line 16-line 23.

Anonymous: "Kernel density estimation", Wikipedia, Nov. 13, 2020 (Nov. 13, 2020), pp. 1-12, XP055895569, Retrieved from the Internet: URL:https://en.wikipedia.org/w/index.php?title=Kernel_density_estimation&oldid=988508333 [retrieved on Jun. 6, 2022].

Anonymous: "openaps / oref0 /lib/determine-basal-js", openaps repository, Nov. 9, 2019 (Nov. 9, 2019), pp. 1-17, XP055900283, Retrieved from the Internet: URL:https://github.com/openaps/oref0/blob/master/lib/determine-basal/determine-basal.js [retrieved on Jun. 6, 2022] line 116-line 118, line 439-line 446.

Anonymous: "AndroidAPS screens", AndroidAPS documentation, Oct. 4, 2020 (Oct. 4, 2020), pp. 1-12, XP055894824, Retrieved from the Internet: URL:https://github.com/openaps/AndroidAPSdocs/blob/25d8acf8b28262b411b34f416f173ac0814d7e14/docs/EN/Getting-Started/Screenshots.md [retrieved on Jun. 6, 2022].

Kozak Milos et al: "Issue #2473 of AndroidAPS", MilosKozak / AndroidAPS Public repository, Mar. 4, 2020 (Mar. 4, 2020), pp. 1-4, XP055900328, Retrieved from the Internet: URL:https://github.com/MilosKozak/AndroidAPS/issues/2473 [retrieved on Jun. 6, 2022].

Medication Bar Code System Implementation Planning Section I: A Bar Code Primer for Leaders, Aug. 2013.

Medication Bar Code System Implementation Planning Section II: Building the Case for Automated Identification of Medications, Aug. 2013.

Villareal et al. (2009) in: Distr. Comp. Art. Intell. Bioninf. Soft Comp. Amb. Ass. Living; Int. Work Conf. Art. Neural Networks (IWANN) 2009, Lect. Notes Comp. Sci. vol. 5518; S. Omatu et al. (Eds.), pp. 870-877.

Fox, Ian G .; Machine Learning for Physiological Time Series: Representing and Controlling Blood Glucose for Diabetes Management; University of Michigan. ProQuest Dissertations Publishing, 2020. 28240142. (Year: 2020).

(56) References Cited

OTHER PUBLICATIONS

International Search Report and Written Opinion for the International Patent Application No. PCT/US2022/012896, dated Apr. 22, 2022, 15 pages.

* cited by examiner

DUAL HORMONE DELIVERY SYSTEM FOR REDUCING IMPENDING HYPOGLYCEMIA AND/OR HYPERGLYCEMIA RISK

BACKGROUND

Drug delivery systems that deliver insulin attempt to deliver insulin that diabetic patients cannot produce naturally. Some of the drug delivery systems attempt to deliver small doses of insulin at periodic intervals. Closed loop control systems may be used to adjust insulin delivery dosages and/or rates. These drug delivery systems generally assume that the insulin sensitivity of all patients is roughly the same. One drawback of many such drug delivery systems is that they inadvertently may drive the patient's blood glucose (BG) level to hypoglycemia levels or to hyperglycemia levels.

SUMMARY

In accordance with an exemplary embodiment, a device includes a communication interface with a glucose monitor for enabling glucose level readings of a user from the monitor to be communicated to the device. The device also includes a storage for storing insulin delivery history and/or glucagon delivery history to the user and a carbohydrate ingestion history of the user. The device additionally includes a delivery device interface with a delivery device for delivery of the insulin and/or glucagon to the user. Further, the device includes processing logic for determining whether the user will experience hypoglycemia and/or whether the user will experience hyperglycemia without further preventive measures based at least on one of the glucose level readings of the user, the insulin delivery history and/or the glucagon delivery history to the user, and a limit on an ability of the delivery device to modify the glucose level of the user over a time period. The processing logic may trigger a preventive measure to modify the glucose level of the user where it is determined that the user will experience hypoglycemia and/or it is determined that the user will experience hyperglycemia without further preventive measures.

The processing logic may trigger the preventive measure of generating an alert that the user will experience hypoglycemia or hyperglycemia. The device may further comprise a video display, and the alert may comprise output displayed on the video display. The device may further comprise an audio output device, and the alert may comprise audio output that is output via the audio output device. The device, in addition to the alert, may cause delivery of a bolus of insulin or glucagon to the user from the delivery device. The processing logic may determine that the user will experience hypoglycemia without preventive measures, and the alert may instruct the user to ingest rescue carbohydrates. The alert may specify a quantity of the carbohydrates for the user to ingest. The triggered preventive measure may be delivery of a bolus of insulin or glucagon from the delivery device.

The processing logic may comprise one of a microprocessor, a field gate programmable array (FPGA), an application specific integrated circuit (ASIC) or a controller integrated circuit. The limit on the device to modify the glucose level of the user may be one of an amount of insulin that can be delivered to the user over a period of time, an amount of glucagon that can be delivered over the period of time or how long can insulin delivery be suspended. The determining whether the user will experience hypoglycemia and/or whether the user will experience hyperglycemia without preventive measures may be additionally based on a carbohydrate ingestion history of the patient.

In accordance with an exemplary embodiment, a method is performed by processing logic of a device. The method includes receiving a glucose monitor reading of a glucose level of a user. The method also includes determining anticipated glucose levels of the user over a future time window based at least on the glucose monitor reading of the glucose level of the user, an amount of insulin already delivered to the user that will affect the glucose level of the user during the future time window, and a limit on an ability of a delivery device to modify the glucose level of the user over a time period. The method additionally includes comparing the determined anticipated glucose levels of the user over the future time window with a hypoglycemic action threshold and/or a hyperglycemic action threshold. Where the comparing indicates that at least one of the determined anticipated glucose levels exceeds a hyperglycemic action threshold, the method triggers an action to reduce the glucose action of the user; and where the comparing indicates that one of the determined anticipated glucose level falls below a hypoglycemic action threshold, the method triggers an action to increase the glucose level of the user.

Where the comparing indicates that at least one of the determined anticipated glucose levels exceeds a hyperglycemic threshold, with the device, a bolus of insulin may be delivered to the user in addition to the generating of an alert that a hyperglycemic event may occur. A dosage of the bolus of insulin to be delivered to bring a glucose level of the user to an acceptable level over the future time window may be determined, and the determined dosage may be delivered to the user by a delivery device. Where the comparing indicates that one of the determined anticipated glucose level falls below a hypoglycemic action threshold, with the device, a bolus of glucagon to the user by a delivery device may occur in addition to the generating an alert that hypoglycemia may occur. The processing logic may implement a closed loop control system for regulating delivery of insulin and/or glucagon to the user. Instructions that cause a processor to perform the method may be stored on a non-transitory computer-readable storage media. The hypoglycemic action threshold may account for a hypoglycemia threshold and an amount suspension of delivery of insulin by the delivery device can reduce the glucose level of the user. The hyperglycemia action threshold may account for the hyperglycemia threshold and a multiple of basal insulin delivery by the delivery device.

DETAILED DESCRIPTION

The exemplary embodiments address the above-described drawback of conventional drug delivery systems. The exemplary embodiments attempt to identify impending hypoglycemia and/or hyperglycemia and take measures to prevent the hypoglycemia or hyperglycemia. Exemplary embodiments may provide a drug delivery system for delivering insulin and glucagon as needed by a user of the drug delivery system. The drug delivery system may deploy a control system that controls the automated delivery of insulin and glucagon to a patient by the drug delivery system. The control system seeks among other goals to avoid the user experiencing hypoglycemia or hyperglycemia. The control system may employ a clinical decision support algorithm as is described below to control delivery of insulin and glucagon to reduce the risk of hypoglycemia or hyperglycemia and to provide alerts to the user when needed. The control system assesses whether the drug delivery system can respond enough to avoid hypoglycemia or hyperglycemia and generates alerts when manual action is needed to avoid hypoglycemia or hyperglycemia. For instance, if a user is at risk of hypoglycemia and the maximum drug delivery system response (such as suspension of insulin delivery or delivery of glucagon) is deemed to be insufficient, an alert may be sent to the user to ingest a certain quantity of carbohydrates.

The control system may use data from a BG sensor, such as a continuous glucose monitor (CGM), and a quantity of insulin already delivered to a user in making decisions regarding drug delivery and alerts. In addition, the control system may consider the operating limits of the drug delivery system and pre-existing carbohydrate ingestion by a user.

Although the drug delivery system may be an artificial pancreas (AP) system that seeks to emulate in part the endocrine behavior of an actual human pancreas, it should be appreciated that the approach described herein is more general and can apply to other drug delivery systems for delivering insulin and/or glucagon. The drug delivery system may employ different types of tubed or tubeless pumps for drug delivery. A closed loop control system may be used in some exemplary embodiments.

Figure 1:
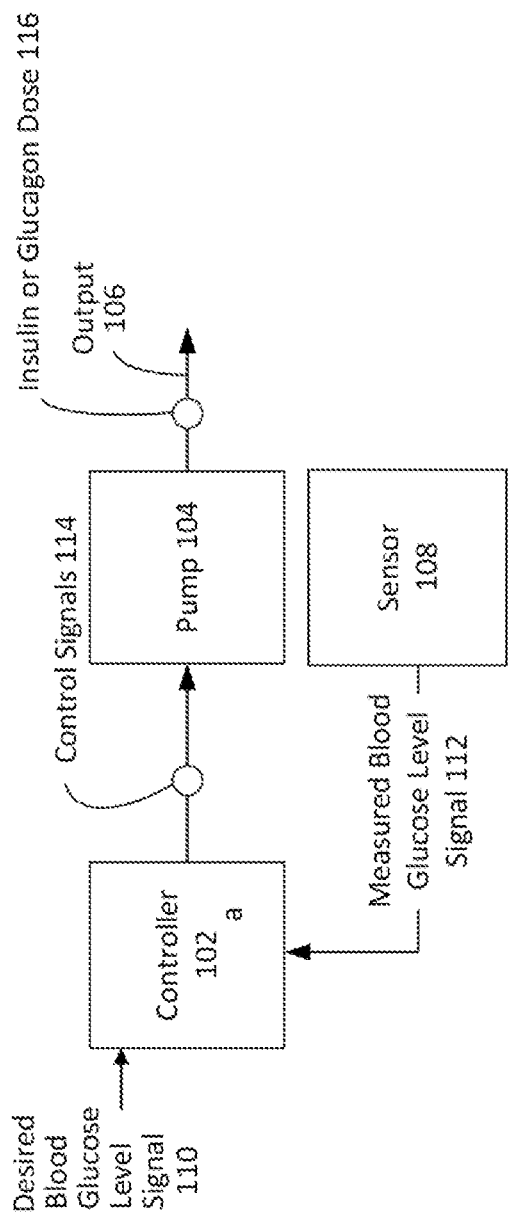
FIG. 1 depicts a simplified diagram of a drug delivery system for practicing an exemplary embodiment.

FIG. 1 illustrates a simplified block diagram of an example of a drug delivery system 100 suitable for practicing an exemplary embodiment. The drug delivery system 100 may not only deliver insulin to the user but also may deliver glucagon to the user. The example drug delivery system 100 may include a controller 102, a pump mechanism or other fluid extraction mechanism 104 (hereinafter "pump 104"), and a sensor 108. The controller 102, pump 104, and sensor 108 may be communicatively coupled to one another via a wired or wireless communication paths. For example, each of the controller 102, the pump 104 and the sensor 108 may be equipped with a wireless radio frequency transceiver operable to communicate via one or more communication protocols, such as Bluetooth®, or the like. The sensor 108 may be a glucose monitor such as, for example, a CGM 108. The CGM 108 may, for example, be operable to measure BG values of a user to generate the measured actual BG level signal 112.

As shown in the example, the controller 102 may receive a desired BG level signal 110, which may be a first signal, indicating a desired BG level or range for a user. The desired BG level signal 110 may be received from a user interface to the controller or other device, or by an approach that automatically determines a BG level for a user. The sensor 108 may be coupled to the user and be operable to measure an approximate value of an actual BG level of the user. The measured BG value, the actual BG level, the approximate measured value of the actual BG level are only approximate values of a user's BG level and it should be understood that there may be errors in the measured BG levels. The errors may, for example, be attributable to a number of factors such as age of the sensor 108, location of the sensor 108 on a body of a user, environmental factors (e.g., altitude, humidity, barometric pressure), or the like. The terms measured BG value, actual BG level, approximate measured value of the actual BG level may be used interchangeably throughout the specification and drawings. In response to the measured BG level or value, the sensor 108 generate a signal indicating the measured BG value. As shown in the example, the controller 102 may also receive from the sensor 108 via a communication path, a measured BG level signal 112, which may be a second signal, indicating an approximate measured value of the actual BG level of the user.

Based on the desired BG level signal 110 and the measured actual BG level signal 112 and additional information as will be described below, the controller 102 may generate one or more control signals 114 for directing operation of the pump 104. For example, one of the control signals 114 may cause the pump 104 to deliver a dose of insulin or glucagon 116 to a user via output 106. The dose of insulin or glucagon 116 may, for example, be determined based on a difference between the desired BG level signal 110 and the actual BG signal level 112 and additional information. The dose of insulin or glucagon 116 may be determined as an appropriate amount to drive the actual BG level of the user to the desired BG level. Based on operation of the pump 104 as determined by the control signals 114, the user may receive the insulin 116 from the pump 104. It should be appreciated that in some embodiments, separate pumps may be provided for the insulin and the glucagon. Moreover, in addition to the control signal to the pump 104, the drug delivery system may generate alerts as will be described below.

In various examples, one or more components of the drug delivery system 100 may be incorporated into a wearable or on body drug delivery system that is attached to the user.

The simplified block diagram of the example drug delivery system 100 provides a general illustration of the drug delivery of the drug delivery system and the feedback loop provided therein. An example of a more detailed implementation of devices usable in such a drug delivery system is illustrated in FIG. 2.

Various examples of a drug delivery system include a wearable drug delivery device that may operate in the system to manage treatment of a diabetic user according to a diabetes treatment plan. The diabetes treatment plan may include a number of parameters related to the delivery of insulin and/or glucagon that may be determined and modified by a computer application referred to as a drug delivery application. This application may also generate alerts as described below.

A wearable drug delivery device as described herein may include a controller operable to direct operation of the wearable drug delivery device via the drug delivery application. For example, a controller of the wearable drug delivery device may provide a selectable activity mode of operation for the user. Operation of the drug delivery device in the activity mode of operation may reduce a probability of hypoglycemia during times of increased insulin sensitivity for the user and may reduce a probability of hyperglycemia during times of increased insulin requirements for the user. The activity mode of operation may be activated by the user or may be activated automatically by the controller. The controller may automatically activate the activity mode of operation based on a detected activity level of the user and/or a detected location of the user.

Figure 2:
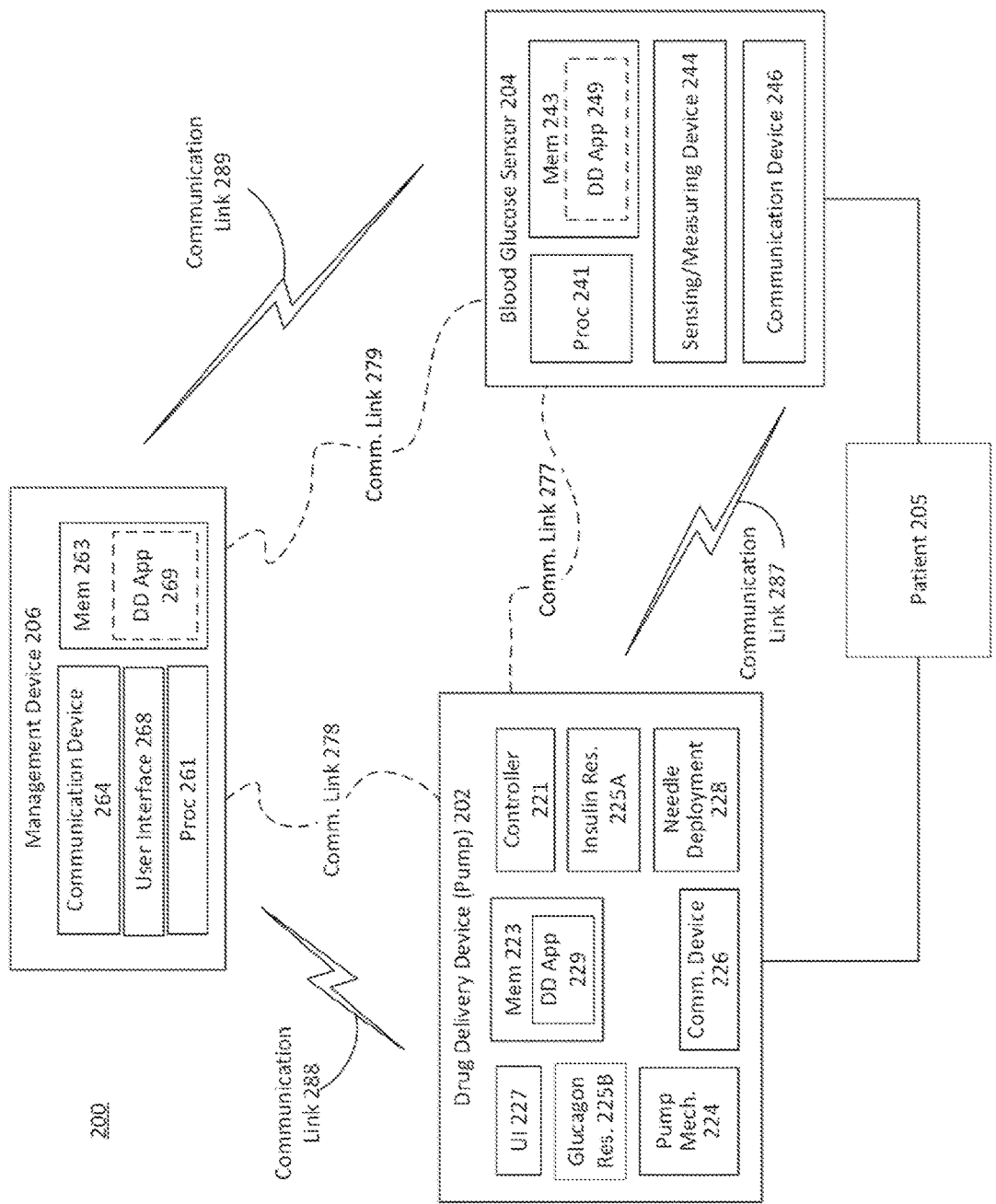
FIG. 2 depicts a more detailed diagram of a drug delivery system for practicing an exemplary embodiment.

FIG. 2 illustrates an example of a drug delivery system 200. The drug delivery system 200 may include a drug delivery device 202, a management device 206, and a BG sensor 204.

In the example of FIG. 2, the drug delivery device 202 may be a wearable or on-body drug delivery device that is worn by a user on the body of the user (designated as patient 205). The drug delivery device 202 may include a pump mechanism 224 that may, in some examples be referred to as a drug extraction mechanism or component, and a needle deployment mechanism 228. In various examples, the pump mechanism 224 may include a pump or a plunger (not shown).

The needle deployment component 228 may, for example include a needle (not shown), a cannula (not shown), and any other fluid path components for coupling the stored liquid drug in the respective reservoirs 225A and 225B to the user 205. Separate reservoirs may be provided for insulin 225A and for glucagon 225B. The cannula may form a portion of the fluid path component coupling the user 205 to one of the reservoirs 225A and 225B. After the needle deployment component 228 has been activated, a fluid path (not shown) to the user is provided, and the pump mechanism 224 may expel a liquid drug from a respective one of the reservoirs 225A or 225B to deliver the liquid drug to the user via the fluid path. The fluid path may, for example, include tubing (not shown) coupling the wearable drug delivery device 202 to the user (e.g., tubing coupling the cannula to the reservoirs 225A and 225B). Separate fluid paths may be provided for the insulin reservoir to the user and the glucagon reservoir to the patient.

The wearable drug delivery device 202 may further include a controller 221 and a communications interface device 226. The controller 221 may be implemented in hardware, software, or any combination thereof. The controller 221 may, for example, be a microprocessor, a logic circuit, a field programmable gate array (FPGA), an application specific integrated circuit (ASIC) or a microcontroller coupled to a memory. The controller 221 may maintain a date and time as well as other functions (e.g., calculations or the like) performed by processors. The controller 221 may be operable to execute a drug delivery algorithm stored in the memory that enables the controller 221 to direct operation of the drug delivery device 202. In addition, the controller 221 may be operable to receive data or information indicative of the activity of the user from the IMU 207, as well as from any other sensors (such as those (e.g., accelerometer, location services application or the like) on the management device 206 or CGM 204) of the drug delivery device 202 or any sensor coupled thereto, such as a global positioning system (GPS)-enabled device or the like.

The controller 221 may provide the alert, for example, through the communications interface device 226. The communications interface device 226 may provide a communications link to one or more management devices physically separated from the drug delivery device 202 including, for example, a management device 206 of the user and/or a caregiver of the user (e.g., a parent). The communication link provided by the communications interface device 226 may include any wired or wireless communication link operating according to any known communications protocol or standard, such as Bluetooth or a cellular standard.

The example of FIG. 2 further shows the drug delivery device 202 in relation to a BG sensor 204, which may be, for example, a CGM. The CGM 204 may be physically separate from the drug delivery device 202 or may be an integrated component thereof. The CGM 204 may provide the controller 221 with data indicative of measured or detected BG levels of the user.

The management device 206 may be maintained and operated by the user or a caregiver of the user. The management device 206 may control operation of the drug delivery device 202 and/or may be used to review data or other information indicative of an operational status of the drug delivery device 202 or a status of the user. The management device 206 may be used to direct operations of the drug delivery device 202 and generate alerts to the user. The management device 206 may include a processor 261 and memory devices 263. The memory devices 262 may store a drug delivery (DD) application 269 including programming code that may implement the functionality described herein. The management device 206 may receive alerts, notifications, or other communications from the drug delivery device 202 via one or more known wired or wireless communications standard or protocol.

The drug delivery system 200 may be operable to implement a DD application. The drug delivery system 200 may be an automated drug delivery system that may include a wearable drug delivery device (pump) 202, a sensor 204, and a personal diabetes management device (PDM) 206.

In an example, the wearable drug delivery device 202 may be attached to the body of a user 205 and may deliver any therapeutic agent, including any drug or medicine, such as insulin or the like, to a user. The wearable drug delivery device 202 may, for example, be a wearable device worn by the user. For example, the wearable drug delivery device 202 may be directly coupled to a user (e.g., directly attached to a body part and/or skin of the user via an adhesive or the like). In an example, a surface of the wearable drug delivery device 202 may include an adhesive to facilitate attachment to a user.

The wearable drug delivery device 202 may be referred to as a pump, or an insulin pump, in reference to the operation of expelling a drug from the reservoirs 225A and 225B for delivery of the drug to the user.

In an example, the wearable drug delivery device 202 may include reservoirs 225A and 225B for storing the drugs (such as insulin and glucagon), a needle or cannula (not shown) for delivering the respective drugs into the body of the user (which may be done subcutaneously, intraperitoneally, or intravenously), and a pump mechanism (mech.) 224, or other drive mechanism, for transferring the drugs from the reservoirs 225A and 225B, through a needle or cannula (not shown), and into the user. The reservoirs 225A and 225B may be configured to store or hold a liquid or fluid, such as insulin, morphine, or another therapeutic drug. The pump mechanism 224 may be fluidly coupled to reservoirs 225A and 225B, and communicatively coupled to the processor 221. The wearable drug delivery device 202 may also include a power source (not shown), such as a battery, a piezoelectric device, or the like, for supplying electrical power to the pump mechanism 224 and/or other components (such as the processor 221, memory 223, and the communication device 226) of the wearable drug delivery device 202. Although also not shown, an electrical power supply for supplying electrical power may similarly be included in each of the sensor 204, the smart accessory device 207 and the management device (PDM) 206.

In an example, the BG sensor 204 may be a device communicatively coupled to the processor 261 or 221 and may be operable to measure a BG value at a predetermined time interval, such as every 5 minutes, or the like. The BG sensor 204 may provide a number of BG measurement values to the drug delivery applications operating on the respective devices. For example, the BG sensor 204 may be a continuous BG sensor that provides BG measurement values to the drug delivery applications operating on the respective devices periodically, such as approximately every 5, 10, 12 minutes, or the like.

The wearable drug delivery device 202 may contain analog and/or digital circuitry that may be implemented as a controller 221 (or processor) for controlling the delivery of the drug or therapeutic agent. The circuitry used to implement the processor 221 may include discrete, specialized logic and/or components, an application-specific integrated circuit, a microcontroller or processor that executes software instructions, firmware, programming instructions or programming code (enabling, for example, the DD application 229 stored in memory 223, or any combination thereof. The memory 223 may store measured glucose levels, insulin delivery history, glucagon delivery history, carbohydrate ingestion history and/or the like. The processor 221 may execute a control algorithm, such as the DD application 229, and other programming code that may make the processor 221 operable to cause the pump to deliver doses of the drugs or therapeutic agents to a user at predetermined intervals or as needed to bring BG measurement values to a target BG value, such as will be described in more detail below. The size and/or timing of the doses may be programmed, for example, into the DD application 229 by the user or by a third party (such as a health care provider, wearable drug delivery device manufacturer, or the like) using a wired or wireless link, such as 220, between the wearable drug delivery device 202 and a management device 206 or other device, such as a computing device at a healthcare provider facility. In an example, the pump or wearable drug delivery device 202 is communicatively coupled to the processor 261 of the management device via the wireless link 220 or via a wireless link, such as 291 from smart accessory device 207 or 208 from the sensor 204. The pump mechanism 224 of the wearable drug delivery device may be operable to receive an actuation signal from the processor 261, and in response to receiving the actuation signal and expel insulin from the reservoirs 225A and 225B and the like.

The devices in the system 200, such as management device 206, smart accessory device 207 and sensor 204, may also be operable to perform various functions including controlling the wearable drug delivery device 202. For example, the management device 206 may include a communication device 264, a processor 261, and a management device memory 263 for storing data, such as insulin delivery history, glucose delivery history, BG level history, alert history, carbohydrate ingestion history and activity history. The management device memory 263 may store an instance of the DD application 269 that includes programming code, that when executed by the processor 261 provides the process examples described herein. The management device memory 263 may also store programming code for providing the process examples described with reference to the examples herein.

Although not shown, the system 200 may include a smart accessory device may be, for example, an Apple Watch®, other wearable smart device, including eyeglasses, provided by other manufacturers, a global positioning system-enabled wearable, a wearable fitness device, smart clothing, or the like. Similar to the management device 206, the smart accessory device (not shown) may also be operable to perform various functions including controlling the wearable drug delivery device 202. For example, the smart accessory device may include a communication device, a processor, and a memory. The memory may store an instance of the AP application that includes programming code for providing the process examples described with reference to the examples described herein. The memory may also as store programming code and be operable to store data related to the AP application.

The sensor 204 of system 200 may be a CGM as described above, that may include a processor 241, a memory 243, a sensing or measuring device 244, and a communication device 246. The memory 243 may store an instance of a DD application 249 as well as other programming code and be operable to store data related to the drug delivery application 249. The DD application 249 may also include programming code for providing the process examples described with reference to the examples described herein.

Instructions for determining the delivery of the drugs or therapeutic agents (e.g., as a bolus dosage) to the user (e.g., the size and/or timing of any doses of the drug or therapeutic agent) may originate locally by the wearable drug delivery device 202 or may originate remotely and be provided to the wearable drug delivery device 202. In an example of a local determination of drug or therapeutic agent delivery, programming instructions, such as an instance of the DD application 229, stored in the memory 223 that is coupled to the wearable drug delivery device 202 may be used to make determinations by the wearable drug delivery device 202. In addition, the wearable drug delivery device 202 may be operable to communicate via the communication device 226 and communication link 288 with the wearable drug delivery device 202 and with the BG sensor 204 via the communication device 226 and communication link 289.

Alternatively, the remote instructions may be provided to the wearable drug delivery device 202 over a wired or wireless link by the management device (PDM) 206. The PDM 206 may be equipped with a processor 261 that may execute an instance of the DD application 269, if present in the memory 263. The memory may store computer-readable instructions for execution by the processor 261. The memory may include a non-transitory computer-readable storage media for storing instructions executable by the processor. The wearable drug delivery device 202 may execute any received instructions (originating internally or from the management device 206) for the delivery of insulin and glucagon to the user. In this way, the delivery of the insulin to a user may be automated.

In various examples, the wearable drug delivery device 202 may communicate via a wireless communication link 288 with the management device 206. The management device 206 may be an electronic device such as, for example, a smart phone, a tablet, a dedicated diabetes therapy management device, or the like. Alternatively, the management device 206 may be a wearable wireless accessory device, such as a smart watch, or the like. The wireless links 287-289 may be any type of wireless link provided by any known wireless standard. As an example, the wireless links 287-289 may enable communications between the wearable drug delivery device 202, the management device 206 and sensor 204 based on, for example, Bluetooth®, Wi-Fi®, a near-field communication standard, a cellular standard, or any other wireless optical or radio-frequency protocol.

The sensor 204 may also be coupled to the user by, for example, adhesive or the like and may provide information or data on one or more medical conditions and/or physical attributes of the user. The information or data provided by the sensor 204 may be used to adjust drug delivery operations of the wearable drug delivery device 202. For example, the sensor 204 may be a glucose sensor operable to measure BG and output a BG value or data that is representative of a BG value. For example, the sensor 204 may be a glucose monitor that provides periodic BG measurements a CGM, or another type of device or sensor that provides BG measurements.

The sensor 204 may include a processor 241, a memory 243, a sensing/measuring device 244, and communication device 246. The communication device 246 of sensor 204 may include an electronic transmitter, receiver, and/or transceiver for communicating with the management device 206 over a wireless link 222 or with wearable drug delivery device 202 over the link 208. The sensing/measuring device 244 may include one or more sensing elements, such as a BG measurement element, a heart rate monitor, a blood oxygen sensor element, or the like. The processor 241 may include discrete, specialized logic and/or components, an application-specific integrated circuit, a microcontroller or processor that executes software instructions, firmware, programming instructions stored in memory (such as memory 243), or any combination thereof. For example, the memory 243 may store an instance of a DD application 249 that is executable by the processor 241.

Although the sensor 204 is depicted as separate from the wearable drug delivery device 202, in various examples, the sensor 204 and wearable drug delivery device 202 may be incorporated into the same unit. That is, in one or more examples, the sensor 204 may be a part of the wearable drug delivery device 202 and contained within the same housing of the wearable drug delivery device 202 (e.g., the sensor 204 may be positioned within or embedded within the wearable drug delivery device 202). Glucose monitoring data (e.g., measured BG values) determined by the sensor 204 may be provided to the wearable drug delivery device 202, smart accessory device 207 and/or the management device 206, which may use the measured BG values to determine movement of the wearable drug delivery device indicative of physical activity of the user, an activity mode, a hyperglycemia mode and a hyperglycemia mode.

In an example, the management device 206 may be a personal diabetes manager. The management device 206 may be used to program or adjust operation of the wearable drug delivery device 202 and/or the sensor 204. The management device 206 may be any portable electronic device including, for example, a dedicated controller, such as processor 261, a smartphone, or a tablet. In an example, the personal management device (PMD) 206 may include a processor 261, a management device management device memory 263, and a communication device 264. The management device 206 may contain analog and/or digital circuitry that may be implemented as a processor 261 (or controller) for executing processes to manage a user's BG levels and for controlling the delivery of the drugs or therapeutic agents to the user. The processor 261 may also be operable to execute programming code stored in the management device management device memory 263. For example, the management device management device memory 263 may be operable to store a DD application 269 that may be executed by the processor 261. The processor 261 may when executing the DD application 269 may be operable to perform various functions, such as those described with respect to the examples. The communication device 264 may be a receiver, a transmitter, or a transceiver that operates according to one or more radio-frequency protocols. For example, the communication device 264 may include a cellular transceiver and a Bluetooth transceiver that enables the management device 206 to communicate with a data network via the cellular transceiver and with the sensor 204 and the wearable drug delivery device 202. The respective transceivers of communication device 264 may be operable to transmit signals containing information useable by or generated by the drug delivery application or the like. The communication devices 226 and 246 of respective wearable drug delivery device 202 and sensor 204, respectively, may also be operable to transmit signals containing information useable by or generated by the drug delivery application or the like.

The wearable drug delivery device 202 may communicate with the sensor 204 over a wireless link 208 and may communicate with the management device 206 over a wireless link 220. The sensor 204 and the management device 206 may communicate over a wireless link 222. The smart accessory device 207, when present, may communicate with the wearable drug delivery device 202, the sensor 204 and the management device 206 over wireless links 287, 288 and 289, respectively. The wireless links 287, 288 and 289 may be any type of wireless link operating using known wireless standards or proprietary standards. As an example, the wireless links 287, 288 and 289 may provide communication links based on Bluetooth®, Wi-Fi, a near-field communication standard, a cellular standard, or any other wireless protocol via the respective communication devices 226, 246 and 264. In some examples, the wearable drug delivery device 202 and/or the management device 206 may include a user interface 227 and 268, respectively, such as a keypad, a touchscreen display, levers, buttons, a microphone, a speaker, a display, or the like, that is operable to allow a user to enter information and allow the management device to output information for presentation to the user.

In various examples, the drug delivery system 200 may be an insulin drug delivery system. For example, the wearable drug delivery device 202 may be the OmniPod® (Insulet Corporation, Billerica, Mass.) insulin delivery device as described in U.S. Pat. Nos. 7,303,549, 7,137,964, or U.S.

Pat. No. 6,740,059, each of which is incorporated herein by reference in its entirety or another type of insulin delivery device.

In the examples, the drug delivery system 200 may implement the embellished AP algorithm (and/or provide drug delivery functionality) to govern or control automated delivery of insulin and glucagon to a user (e.g., to maintain euglycemia—a normal level of glucose in the blood). The drug delivery application may be implemented by the wearable drug delivery device 202 and/or the sensor 204. The drug delivery application may be used to determine the times and dosages of insulin and glucagon delivery. In various examples, the drug delivery application may determine the times and dosages for delivery based on information known about the user, such as the user's sex, age, weight, or height, and/or on information gathered about a physical attribute or condition of the user (e.g., from the sensor 204). For example, the drug delivery application may determine an appropriate delivery of insulin or glucagon based on glucose level monitoring of the user through the sensor 204. The drug delivery application may also allow the user to adjust insulin or glucagon delivery. For example, the drug delivery application may allow a user to select (e.g., via an input) commands for output to the wearable drug delivery device 202, such as a command to set a mode of the wearable drug delivery device, such as an activity mode, a hyperglycemia protect mode, a hypoglycemia protect mode, deliver an insulin bolus, deliver a glucagon bolus or the like. In one or more examples, different functions of the drug delivery application may be distributed among two or more of the management device 206, the wearable drug delivery device (pump) 202 or the sensor 204. In other examples, the different functions of the drug delivery application may be performed by one device, such the management device 206, the wearable drug delivery device (pump) 202 or the sensor 204. In various examples, the drug delivery system 200 may include features of or may operate according to functionalities of a drug delivery system as described in U.S. patent application Ser. No. 15/359,187, filed Nov. 22, 2016 and Ser. No. 16/570,125, filed Sep. 13, 2019, which are both incorporated herein by reference in their entirety.

As described herein, the drug delivery system 200 or any component thereof, such as the wearable drug delivery device may be considered to provide embellished AP functionality or to implement a drug delivery application. Accordingly, references to the drug delivery application (e.g., functionality, operations, or capabilities thereof) are made for convenience and may refer to and/or include operations and/or functionalities of the drug delivery system 200 or any constituent component thereof (e.g., the wearable drug delivery device 202 and/or the management device 206). The drug delivery system 200—for example, as an insulin delivery system implementing an drug delivery application—may be considered to be a drug delivery system or a drug delivery system that uses sensor inputs (e.g., data collected by the sensor 204).

In an example, the drug delivery device 202 includes a communication device 264, which as described above may be a receiver, a transmitter, or a transceiver that operates according to one or more radio-frequency protocols, such as Bluetooth, Wi-Fi, a near-field communication standard, a cellular standard, that may enable the respective device to communicate with the cloud-based services 211. For example, outputs from the sensor 204 or the wearable drug delivery device (pump) 202 may be transmitted to the cloud-based services 211 for storage or processing via the transceivers of communication device 264. Similarly, wearable drug delivery device 202, management device 206 and sensor 204 may be operable to communicate with the cloud-based services 211 via the communication link 288.

In an example, the respective receiver or transceiver of each respective device 202, 206 or 207 may be operable to receive signals containing respective BG measurement values of the number of BG measurement values that may be transmitted by the sensor 204. The respective processor of each respective device 202, 206 or 207 may be operable to store each of the respective BG measurement values in a respective memory, such as 223, 263 or 273. The respective BG measurement values may be stored as data related to the drug delivery, such as 229, 249, or 269. In a further example, the drug delivery application operating on any of the management device 206, the smart accessory device 207, or sensor 204 may be operable to transmit, via a transceiver implemented by a respective communication device, 264, 274, 246, a control signal for receipt by a wearable drug delivery device. In the example, the control signal may indicate an amount of insulin to be expelled by the wearable drug delivery device 202.

In an example, one or more of the devices 202, 204, or 206 may be operable to communicate via a wired communication links 277, 278 and 279, respectively. The cloud-based services (not shown) may utilize servers and data storage (not shown). A communication link that couples the drug delivery system 200 to the cloud-based services may be a cellular link, a Wi-Fi link, a Bluetooth link, or a combination thereof, that is established between the respective devices 202, 204, or 206 of system 200. For example, the data storage (not shown) provided by the cloud-based services may store anonymized data, such as user weight, BG measurements, age, meal carbohydrate information, or the like. In addition, the cloud-based services 211 may process the anonymized data from multiple users to provide generalized information related to the various parameters used by the drug delivery application. For example, an age-based general target BG value related to activity levels or particular exercises or sports may be derived from the anonymized data, which may be helpful when a user selects an activity mode (or a hyperglycemia protect mode, or a hypoglycemia protect modes) or the system 200 automatically implements the activity mode (or the hyperglycemia protect, or the hypoglycemia protect modes). The cloud-based services may also provide processing services for the system 200, such as performing a process described with reference to later examples.

The wearable drug delivery device 202 may also include a user interface 227. The user interface 227 may include any mechanism for the user to input data to the drug delivery device 202, such as, for example, a button, a knob, a switch, a touch-screen display, or any other user interaction component. The user interface 227 may include any mechanism for the drug delivery device 202 to relay data to the user and may include, for example, a display, a touch-screen display, an audio output device or any means for providing a visual, audible, or tactile (e.g., vibrational) output (e.g., as an alert). The user interface 227 may also include additional components not specifically shown in FIG. 2 for sake brevity and explanation. For example, the user interface 227 may include a one or more user input or output components for receiving inputs from or providing outputs to a user or a caregiver (e.g., a parent or nurse), a display that outputs a visible alert, a speaker that outputs an audible, or a vibration device that outputs tactile indicators to alert a user or a caregiver of a potential activity mode, a power supply (e.g., a battery), and the like. Inputs to the user interface 227 may, for example, be a via a fingerprint sensor, a tactile input sensor, a button, a touch screen display, a switch, or the like. In yet another alternative, the activity mode of operation may be requested through a management device 206 that is communicatively coupled to a controller 221 of the wearable drug delivery device 202. In general, a user may generate instructions that may be stored as user preferences in a memory, such as 223 or 263 that specify when the system 200 is to enter the activity mode of operation.

Various operational scenarios and examples of processes performed by the system 200 are described herein. For example, the system 200 may be operable to implement process examples related to an activity mode including a hyperglycemia protect mode and a hypoglycemia protect mode as described in more detail below.

In an example, the drug delivery device 202 may operate as an embellished AP system (e.g., as a portion of the drug delivery system 100) and/or may implement techniques or an algorithm via a drug delivery application that controls and provides functionality related to substantially all aspects of a drug delivery system or at least portions thereof. The drug delivery device 202 may operate in an open-loop or closed-loop manner for providing a user with insulin and glucagon.

Additional features may be implemented as part of the drug delivery application, such as the activity mode, the hyperglycemia mode, the hypoglycemia mode, or the like. For example, the drug delivery device 202 when programming code is executed that enables the activity mode, hyperglycemia mode, hypoglycemia mode or the like of the drug delivery application. As the AP embellished application including the programming code for the activity mode, the hyperglycemia mode, and the hypoglycemia mode is executed, the drug delivery application may adjust operations, such as detecting motion or movement of the wearable drug delivery device that is indicative of physical activity of the user. For example, motion and movement of the wearable drug delivery device 202 that induces motions characteristic of physical activity of the user (e.g., movements, such as jumping, dancing, running, weightlifting, cycling or the like) may be detected by the IMU 207. In addition, the IMU 207, as described with reference to FIG. 3, may include a global positioning system that may detect a location of the wearable drug delivery device 202. Alternatively, or in addition, the wearable drug delivery device 202 may also utilize Wi-Fi location services to determine the location of the wearable drug delivery device 202. For example, the drug delivery algorithm may learn from repeated interaction with the user who may input an indication at particular times that they are about to perform physical activity. Alternatively, or in addition, the wearable drug delivery device 202 may upon detection of a particular location (e.g., gym, sports field, stadium, track, or the like) determine that the user is about to increase their physical activity.

As was mentioned above, the drug delivery system 200 may take steps to assess a risk of hypoglycemia and/or hyperglycemia and take preventive measures to attempt to avoid hypoglycemia or hyperglycemia. The assessment may look at the BG level of the user, the insulin on board for the user, the limit of the automated drug delivery system response and other values such as previously ingested carbohydrates. Based on the assessment, the drug delivery system 200 may deliver insulin or glucagon to a user or may suspend delivery of insulin to the user. Where the assessment indicates that the system limits prevent complete remediation of imminent hypoglycemia or hyperglycemia, the system may generate alerts that instruct the user to take manual action. In some instances, only alerts are generated without system action. In other instances where the system limits are not exceeded, no alerts may be produced; rather the system simply may perform the drug delivery or suspend drug delivery.

Figure 3:
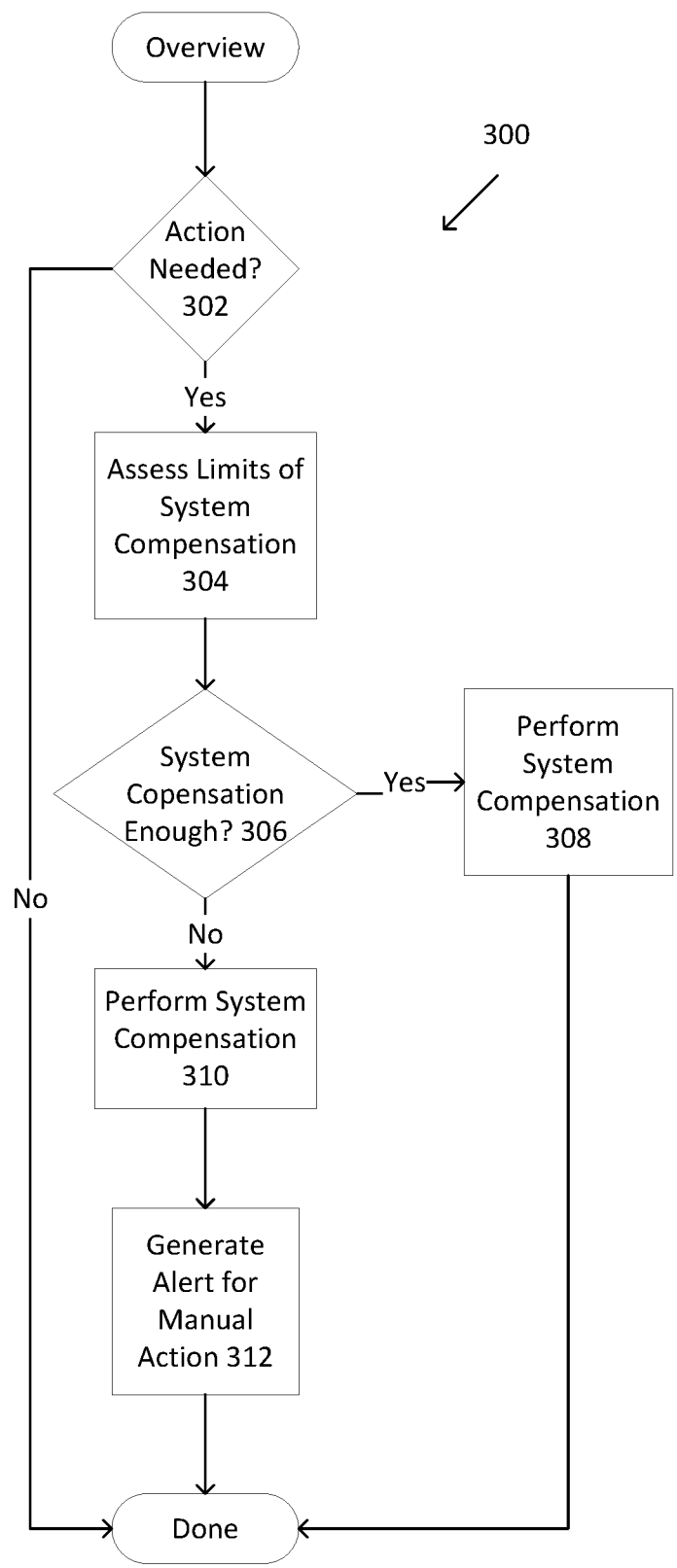
FIG. 3 depicts a flowchart of illustrative steps for reducing risk of hypoglycemia and/or hyperglycemia with a drug delivery system.

FIG. 3 depicts a flowchart 300 of illustrative steps that may be performed in an exemplary embodiment. The drug delivery system initially assesses whether any action is needed (302). The assessment largely is a determination of whether hypoglycemia or hyperglycemia is imminent for the user without additional preventive measures being taken separate from standard basal insulin delivery to the user. The drug delivery system then determines the limits of the system compensation (304). This may include determining how much insulin or glucagon can be delivered in bolus form, how much basal insulin is going to be delivered and how long can insulin delivery be suspended relative to current BG levels and target BG levels. The system determines whether the system compensation suffices to reach the target glucose level (306). If the system compensation suffices, then the system compensation may be performed (308). If the system compensation does not suffice, the system response may still be performed (310) to adjust the BG level of the user closer to the target BG level. This step may be optional. In addition, an alert may be generated to prompt manual action by the user to take remedial measures, such as carbohydrate ingestion, manual insulin or glucagon injection, or simply to inform the user of the risk so that the user can contact medical personnel or the like (312).

Figure 4:
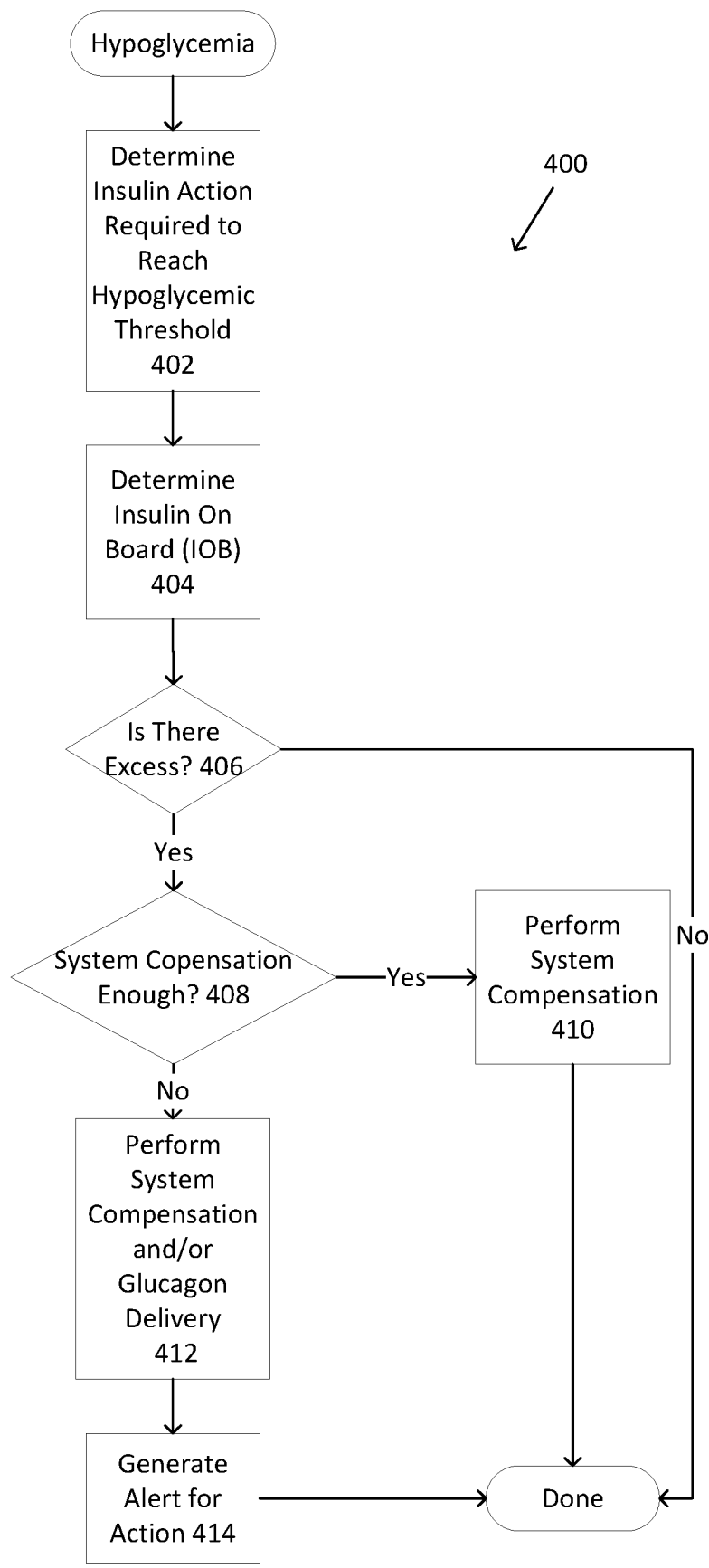
FIG. 4 depicts a depicts a flowchart of illustrative steps for reducing risk of hypoglycemia with a drug delivery system.

FIG. 4 depicts a flowchart 400 of illustrative steps that may be performed for the case of a hypoglycemia risk. These steps may be performed on an ongoing basis when new BG readings take place or only when certain ranges of BG levels are obtained. First, the drug delivery system determines the insulin action required to bring the BG level of the patient to the hypoglycemic threshold from the current BG level reading (402). This determination may entail calculating the following equation:

$$IOB_{hypo} = \frac{CGM(t) - \text{threshold}_{hypo}}{1800/TDI}$$

where $IOB_{hypo}$ is the amount of insulin onboard required to result in the insulin action to bring the BG level of the user to the hypoglycemic threshold; $CGM(t)$ is the BG level at time t; $\text{threshold}_{hypo}$ is the hypoglycemic blood threshold; and TDI is the total daily insulin needs of the user. The above equation determines the difference in BG level between the current BG level and the hypoglycemic threshold BG level. Then, the equation divides this difference by a factor indicative of a heuristic value of the user's correction factor that specifies the amount of drop in glucose concentration (mg/dL) for 1 U of insulin. It should be appreciated that the coefficient 1800 has been use but other coefficient values may be used instead. For instance, a value that is personalized to the user may be used.

The system determines the insulin on board (IOB) for the user to capture the currently remaining insulin action within the user (404). The IOB captures the basal insulin delivered as well as bolus deliveries. The IOB may also be adjusted for carbohydrate ingestion as will be described below. A determination is made whether the IOB is excessive such that the hypoglycemic threshold will be reached (406). This determination may entail calculating:

$$IOB_{excess} = IOB(t) - IOB_{hypo}$$

where the excess $IOB_{excess}$ is the excess value. A positive value indicates that the hypoglycemic threshold will be reached. A negative number indicates that the hypoglycemic threshold will not be reached and no further steps are needed.

Figure 5:
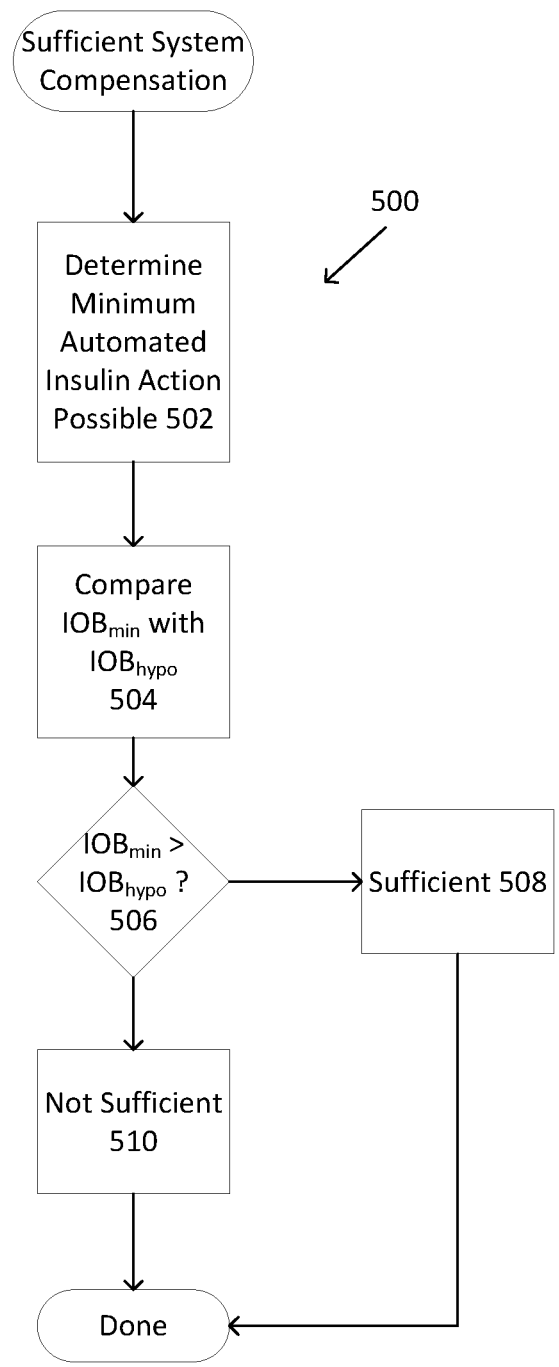
FIG. 5 depicts a flowchart of illustrative steps for determining whether a system response of a drug delivery system is sufficient to avoid a hypoglycemic risk.

If $IOB_{excess}$ is positive, the drug delivery system checks whether the system compensation will be sufficient (408). In this instance, the system compensation may be suspension of basal insulin delivery for a fixed period of time, such as an hour. FIG. 5 depicts a flowchart 500 of steps that may be performed to determine if the possible system compensation is sufficient. First, the system determines the minimum automated insulin action possible (502). This may be, for example, the insulin action resulting from suspending the delivery of automated insulin deliveries in a closed loop control system for an hour. This value may be calculated as:

$$IOB_{min} = IOB(t) - \frac{TDI}{48}$$

where $IOB_{min}$ is the minimum automated insulin action possible; IOB(t) is the insulin on board at time t; and TDI/48 is the total daily insulin of the user divided by 48 to obtain the amount of insulin that is delivered automatically in an hour assuming that the automated deliveries account for half of the TDI.

The $IOB_{min}$ value is the compared with $IOB_{hypo}$ to determine if the suspension of the automated delivery is enough to avoid hypoglycemia for the user (504). If $IOB_{min}$ is greater than $IOB_{hypo}$ (506), the suspension suffices (508); otherwise, the suspension does not suffice (510).

Figure 6:
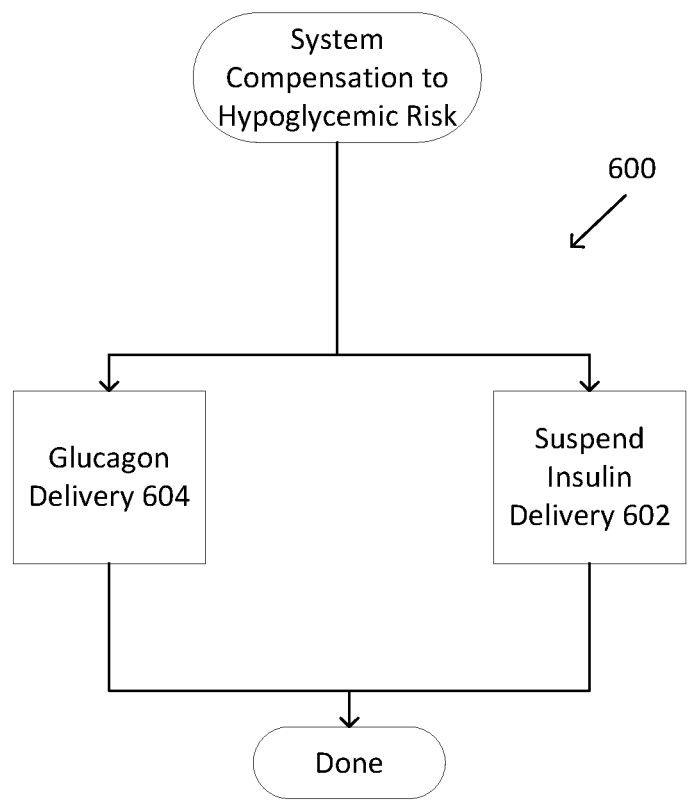
FIG. 6 depicts a diagram of possible system responses to a hypoglycemic risk.

FIG. 6 shows possible forms of system compensation for hypoglycemia (600). As was discussed above, one form of response is to suspend automated insulin delivery (602). It should be appreciated that in some exemplary embodiments, the system compensation also may include automated glucagon deliveries (604) as will be described below and not just suspension of insulin delivery. The extent that such automated glucagon deliveries may alter the BG level of the patient may be part of the calculus to determine if the system response is sufficient.

Hence, if the system compensation suffices (408), the system compensation is performed (410). In this case, the automated insulin delivery is suspended for a preset time, such as an hour, to prevent the user BG level reaching the hypoglycemia threshold. However, if the system response is not sufficient, the system compensation may still be performed to assist in increasing the BGlevel of the patient (412). This step may be optional in some instances. However, an alert may be generated to have action performed (414). The action may be an automated action, such as the suspension of automated insulin delivery or an automated delivery of glucagon. In that instance, the alert serves to inform the user of the automated action. However, the alert may relate to manual action that is requested of the user. These alerts may be referred to as manual risk alerts.

Figure 7:
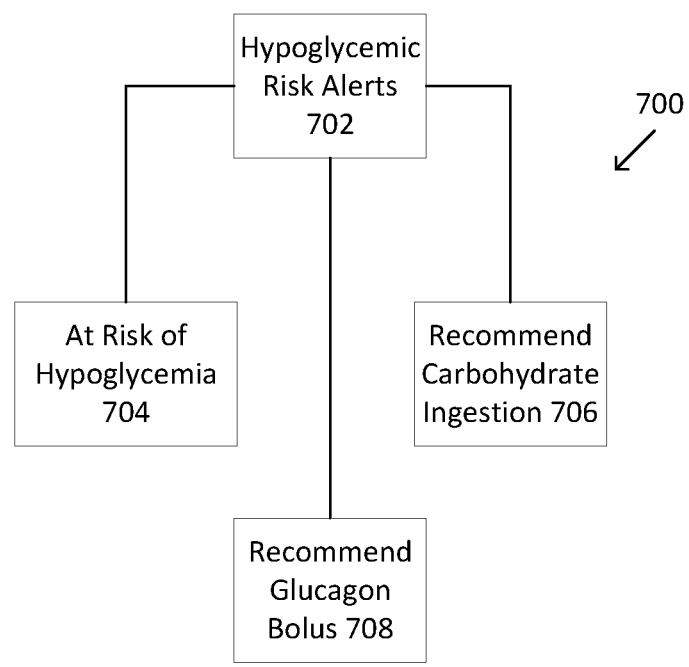
FIG. 7 depicts a diagram showing illustrative types of hypoglycemic risk alerts.

The manual hypoglycemic risk alerts (702) may take different forms as depicted in the diagram 700 of FIG. 7. A basic alert (704) simply may advise the user of the hypoglycemic risk. This type of alert (704) may prompt the user to take preventive measures or contact medical personnel. Another variety of alert may prompt the user to take a specific action, such as ingestion of a given quantity of carbohydrates (706). The amount of carbohydrates ingested may be calculated as:

$$CHO_{rec} = IOB_{excess} \cdot ICR$$

where ICR refers to the user's insulin to carbohydrate ratio. Yet another alert may prompt the user to manually deliver a glucagon bolus of a specified dose (708). The amount of glucagon delivery may be calculated as:

$$Glu(t) = \frac{IOB_{excess}(t)}{b(t) \cdot 1h} \cdot 0.04 \frac{W}{B}$$

where Glu(t) is the recommended glucagon delivery, in mg, for the current time t; $IOB_{excess}(t)$ is the user's current excess insulin on board; b(t) is the user's current basal profile entry; W is the user's bodyweight, in kilograms; and B is a standard baseline bodyweight for which the ratio between 1 basal hour rate delivery and 0.04 mg of glucagon delivery are equivalent. There may be other varieties of alerts and alert types may be combined.

Figure 8:
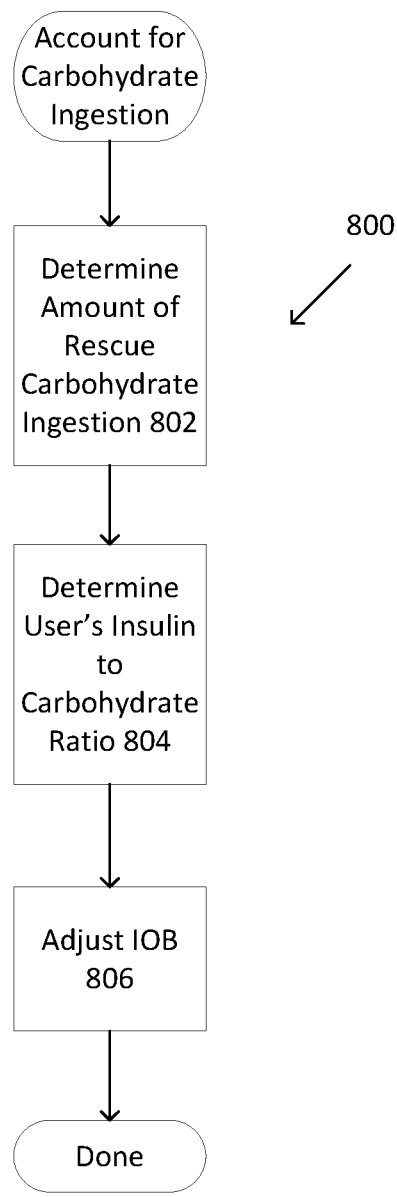
FIG. 8 depicts a flowchart of illustrative steps for accounting for carbohydrate ingestion in adjusting insulin on board (IOB) for a user.

The above-described approach may be expanded to incorporate any pre-existing carbohydrate ingestion to better inform the estimate of pre-existing insulin delivery in the IOB estimate. As shown in the flowchart 800 of FIG. 8, the first step is to determine the sum of rescue carbohydrate ingestion (802). The following equation determines the sum of rescue carbohydrate ingestion over a time scale, assuming a linear decay:

$$CHO_m(i) = \sum_{k=i}^{i-t_m} \left(1 - \frac{t_k - t_m}{5}\right) CHO(k)$$

Where $CHO_m(i)$ is the sum of carbohydrate ingestion, k is an index of rescue carbohydrate ingestion events, CHO (k) is the amount of carbohydrates ingested at the kth ingestion, $t_k$ is the time of the kth ingestion event and $t_m$ is the time of the first rescue carbohydrate ingestion.

The user's insulin to carbohydrate ratio may be determined (804). This value may be calculated as:

$$ICR = \frac{450}{TDI}$$

where ICR is the user's insulin to carbohydrate ratio, TDI is the user's total daily insulin, and 450 is a heuristic coefficient. Given the ICR, IOB for the user may be adjusted to account for the rescue carbohydrate ingestion (806). One possible equation for the adjustment is:

$$IOB(t) = IOB_{before\,CHO} - \frac{CHO_m}{ICR}$$

where $IOB_{before\,CHO}$ is the IOB before accounting for the rescue carbohydrate ingestion. The equation determines the reduction in insulin due to the amount of carbohydrate ingestion with linear decay given the insulin to carbohydrate ratio of the user.

Figure 9:
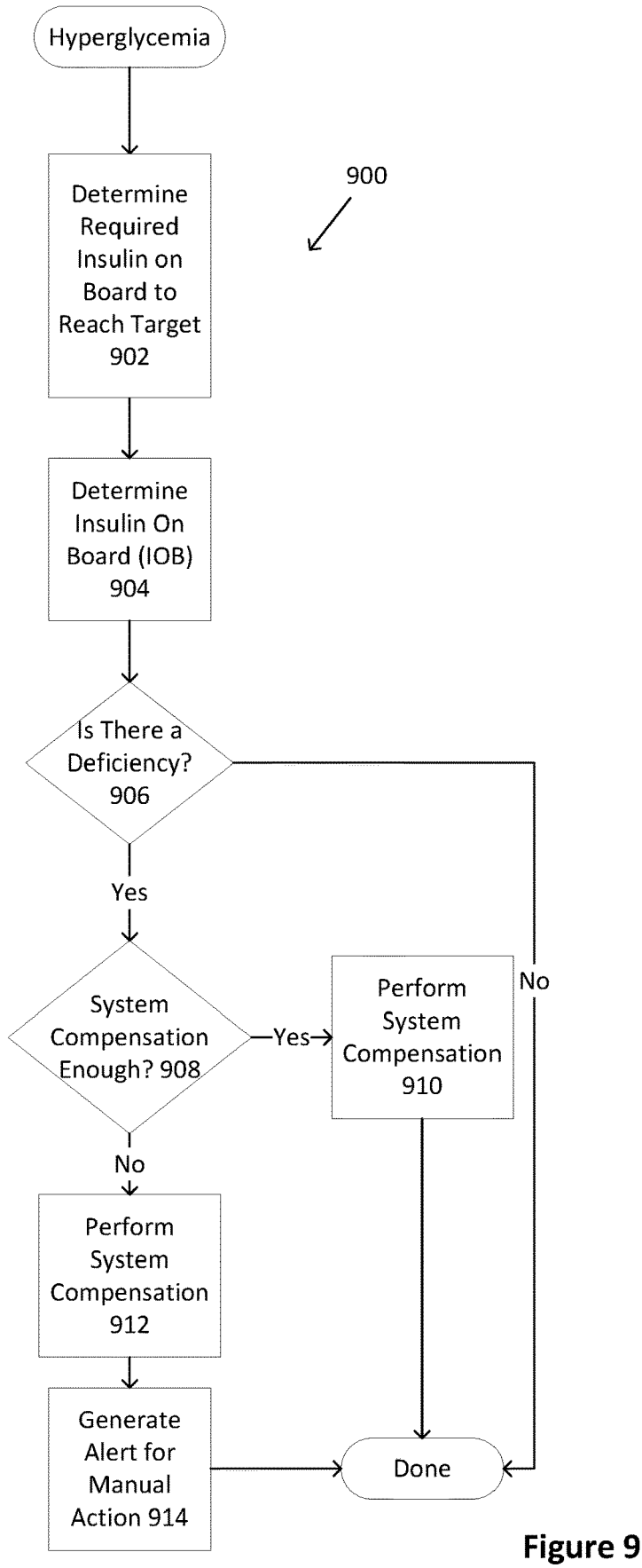
FIG. 9 depicts a depicts a flowchart of illustrative steps for reducing risk of hyperglycemia with a drug delivery system.

As was mentioned above, the clinical decision support algorithm of the drug delivery system not only seeks to reduce the risk of hypoglycemia but also seeks to reduce the risk of hyperglycemia. FIG. 9 provides a flowchart 900 depicting illustrative steps that may be performed to avoid hyperglycemia. These steps may be performed at any time. For instance, they may be performed each time a new BG level reading for a user is received or only when the BG level is in a defined range, such as above a target threshold. Initially, the drug delivery system determines the insulin action required to bring the user to the target threshold (902).

Figure 10:
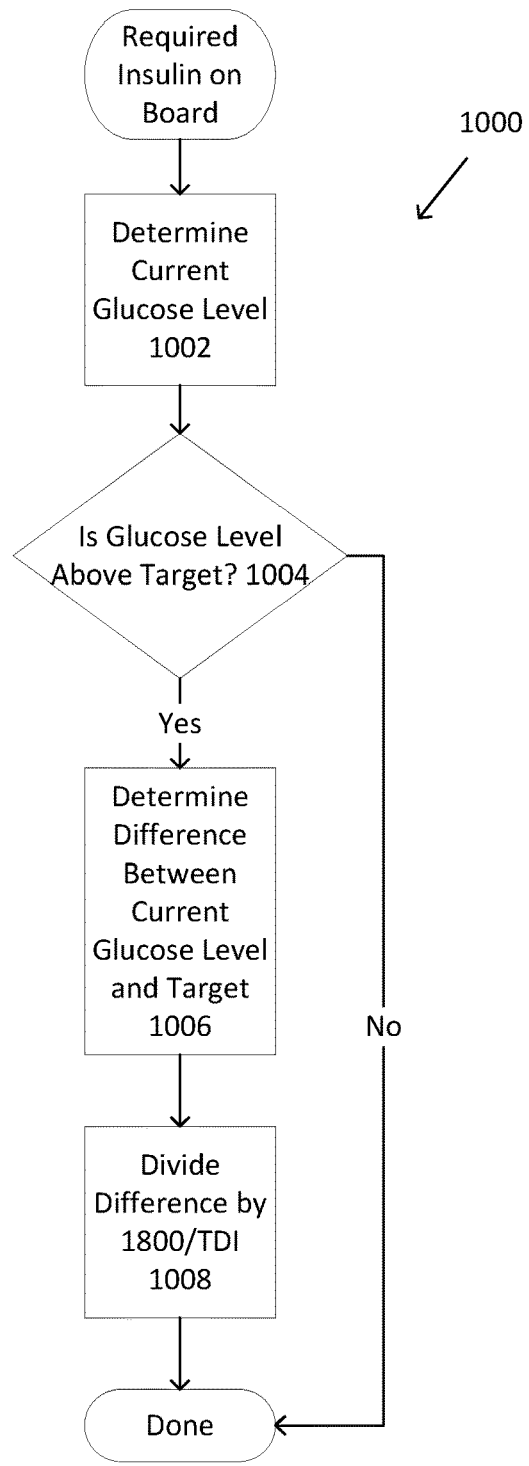
FIG. 10 depicts a flowchart of illustrative steps that may be performed to determine a required amount of IOB for a user to avoid hyperglycemia.

FIG. 10 provides a flowchart 100 of illustrative steps that may be performed to determine the insulin action required to reach target (see step 902). First, the current glucose level of the user is determined at time t (1002). This is referred to as CGM(t). A check is made whether CGM(t) is above the target(t) (1004). This check may be made by calculating CGM(t)–target(t) and determining if it is positive value (1006). The value of this difference represents the magnitude of how much glucose the insulin action must account process. The difference may then be used to determine how much insulin is required to reduce the BG level of the user to the target. One way to determine the amount of insulin is to divide the difference by 1800/TDI (1008). Thus, the insulin action required may be calculated as:

$$IOB_{req} = \frac{CGM(t) - \text{target}(t)}{1800/TDI}$$

where $IOB_{req}$ is the insulin on board required to bring the current BG level CGM(t) to the target threshold target(t) at time t. The 1800/TDI value applies the 1800 rule to determine the amount of insulin necessary to move the BG level to the target.

The drug delivery system determines the IOB(t) for the user (904) and then determines if the IOB(t) suffices to reach the target target(t) (906). This can be expressed as an equation as:

$$IOB_{deficiency} = IOB_{req} - IOB(t)$$

where $IOB_{deficiency}$ refers to the deficiency in insulin to reach the target. A positive value indicates that there is a deficiency, whereas a negative value indicates that there is no deficiency. If there is no deficiency, the IOB(t) suffices, and there is no need for further preventive measures. However, if there is a positive value, the IOB(t) does not suffice and action should be taken.

Figure 11:
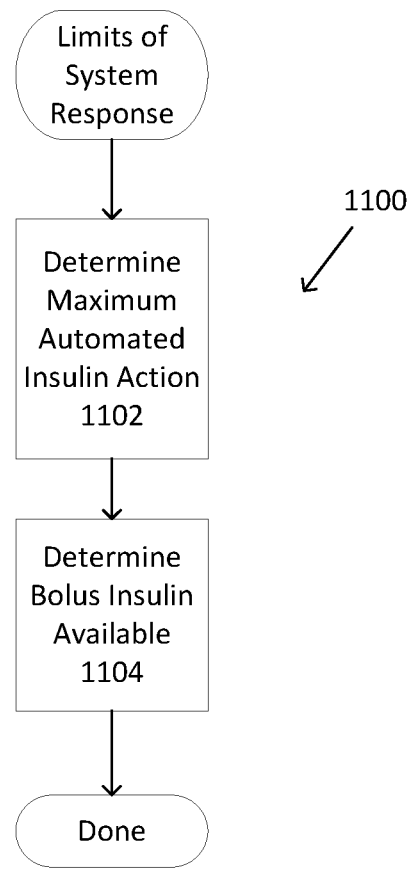
FIG. 11 depicts a flowchart of illustrative steps that may be performed to determine limits of a system response to a hyperglycemic risk.

If there is a deficiency (906), a determination is made whether the limits of the system compensation suffice (908). FIG. 11 depicts a flowchart (1100) of illustrative steps for determining the limits of the system compensation. The system may examine multiple types of system compensation. First, the system may look at whether the maximum automated insulin action by the drug delivery device (1102). The determination of the maximum automated insulin action is described in more detail below relative to FIG. 12. The maximum automated insulin action may suffice to address the hyperglycemia risk by bringing the BG level of the user to the target level. The system may also look at the delivery of an insulin bolus and determine how much insulin may be delivered by a bolus (1104). The delivery of an insulin bolus may be constrained by parameters such as when was a last insulin bolus delivered, the size of the bolus and the available insulin supply. The combination of the two amounts determined in steps (1102) and (1104) may specify the limits of the system compensation. It should be appreciated that in some embodiments these steps (1102) and (1104) need not be performed; rather a single step may be performed. For example, the drug delivery system may only look at the automated insulin action and not consider the bolus insulin delivery options or vice versa.

Figure 12:
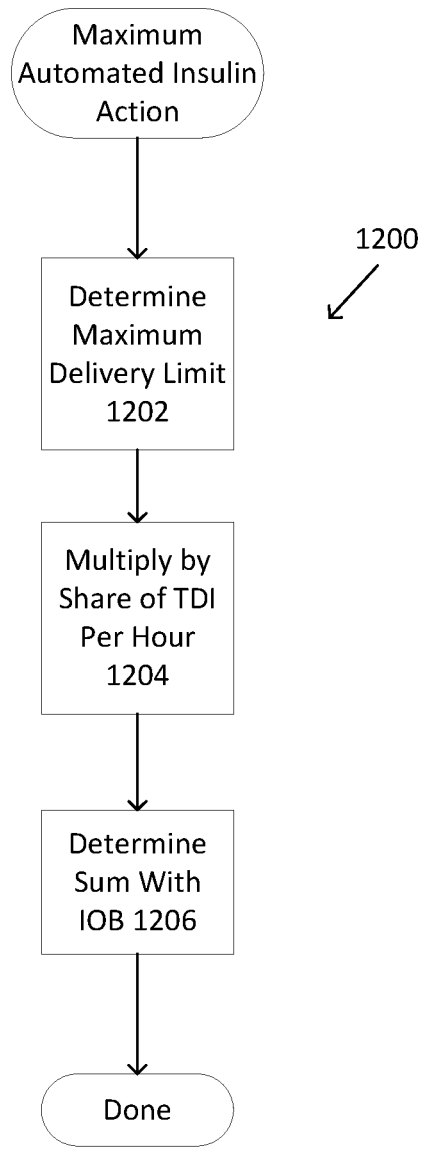
FIG. 12 depicts a flowchart of illustrative steps that may be performed to determine a maximum automated insulin action over a time period for a drug delivery system.
Figure 13:
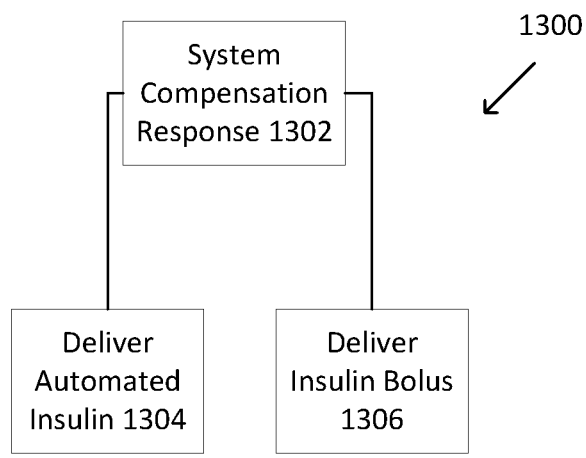
FIG. 13 depicts a diagram depicting illustrative types of system compensation responses for a hyperglycemic risk.
Figure 14:
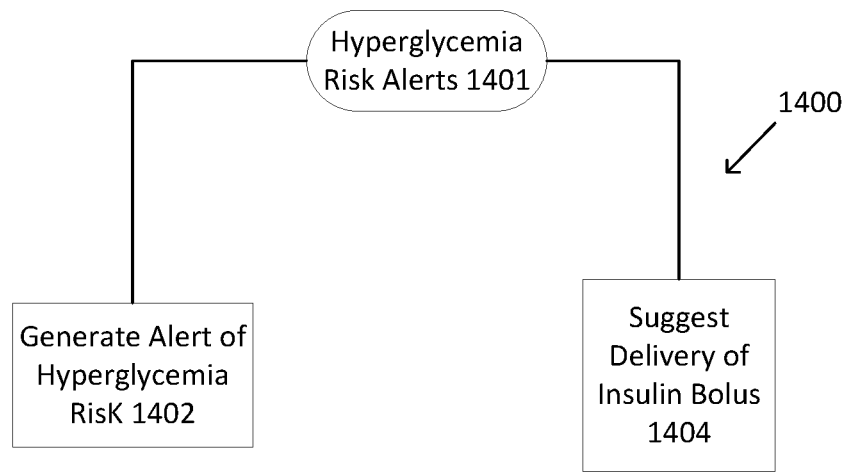
FIG. 14 depicts a diagram of illustrative types of hyperglycemic risk alerts.

FIG. 12 depicts a flowchart (1200) of illustrative steps for determining the maximum automated insulin action (see 1102). The system determines the maximum delivery limit of insulin per day (1202). This is for the case where the drug delivery system is a closed loop system. In other words, a determination is made of how much insulin will the closed loop system allow to be delivered over a time window, such as one hour. The system multiplies the maximum delivery limit by the share of TDI in an hour to establish how much insulin can be delivered in an hour (1204). The resulting product may be summed with the insulin on board IOB(t) to get at the maximum automated insulin action (1206). The total equation may be expressed as:

$$IOB_{max} = IOB(t) + \text{mult}(t)\frac{TDI}{48}$$

where $IOB_{max}$ is the maximum automated insulin for the next hour; IOB(t) is the insulin on board at time t and mult(t) is the maximum delivery limit of insulin.

Where the system compensation suffices (see 908), the system compensation is performed (910). The system compensation (1302) may take the forms of diagram (1300) in FIG. 13. The system compensation response may entail automated delivery of insulin (1304). The dose amount may be increased responsive to the BG level of the user being above target. Alternatively, the basal dosage amount may be delivered if it will suffice to reduce the BG level of the user to target. The system compensation response may include delivering a bolus dose of insulin (1306). The bolus may be delivered in conjunction with the automated delivery of insulin.

Where the system compensation response is not enough, the system compensation may still be performed as described above in some instances (912). In other instances, the system compensation may be skipped. The drug delivery system may also issue alerts to the user (914). FIG. 14 shows a diagram (1400) depicting illustrative hyperglycemic risk alerts (1401) that may be issued. The alert may be informative of the impending hyperglycemic risk (1402). The alert may suggest that the user manually deliver an insulin bolus of a specified dosage (1404). It will be appreciated that other types of alerts may be generated and that the types of alerts may be combined.

Figure 15:
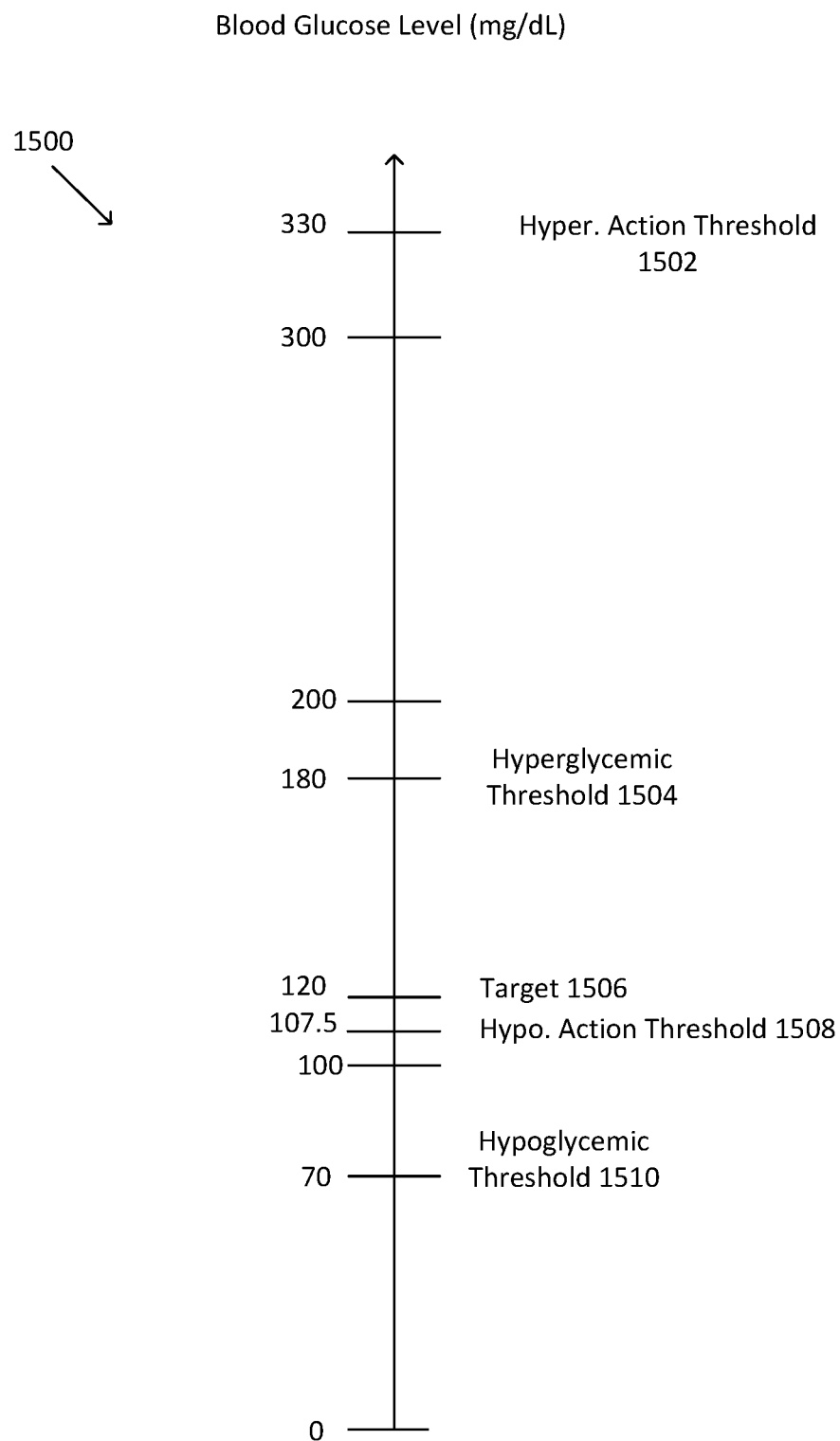
FIG. 15 depicts an illustrative blood glucose level scale showing thresholds that may be used by exemplary embodiments.

In one exemplary embodiment, the clinical decision support algorithm can also incorporate the value and trend of the current glucose values and enable the recommendations if a specific threshold or additional conditions are met while the users are in closed loop. For example, the threshold can also be set to only activate the alert if additional safety constraints are exceeded. For example (as shown in FIG. 15), with an assumed maximum insulin delivery action of 4 times basal and a glucose target 1506 of 120 mg/dL, the hyperglycemia user action recommendation may only occur above a glucose concentration of 330 mg/dL (see hyperglycemic action threshold 1502) versus a hypoglycemic threshold 1504 of 180 mg/dL. As a further example, if the hypoglycemic threshold 1510 is set to 70 mg/dL, the hypoglycemia user action recommendation may only occur below a glucose concentration of 107.5 mg/dL (see 1508). These thresholds can be utilized by assessing the maximum action that can be taken by an automated insulin delivery algorithm in response to changes in the user's glucose concentrations. For instance, given the safety constraints, the algorithm can suspend insulin delivery as the user's glucose concentration is reduced. In this example, this suspension by the algorithm can occur over one hour.

Typical heuristic rules of thumb can be utilized to determine the impact of basal insulin delivery on the user's glucose concentrations. In standard cases, 50% of the user's total daily insulin (TDI) needs can be assumed to cover the user's basal needs (b), with the other 50% covering the user's bolusing needs. The resulting value shows the basal needs throughout the day, which can be converted to the basal needs per hour by dividing this quantity by the number of hours per day. This value can be related to the heuristic rules of thumb for assessing the user's correction factor (CF), or mg/dL change per U of insulin, which is also based on the TDI. Thus, the value of the TDI is canceled, and regardless of the value of the TDI, the implication is that one hour of insulin delivery equivalent to the user's basal results in a change in user's glucose concentration of 37.5 mg/dL. This can be found in the equation below.

$$b*CF = \frac{TDI}{48} * \frac{1800}{TDI} = \frac{1800}{48} = 37.5$$

Consequently, insulin suspension by the algorithm for one hour can compensate for 37.5 mg/dL of glucose drop; therefore, recommendation for user action may only need to occur if a drop that cannot be compensated by insulin suspension will result in user's glucose reaching hypoglycemic risk, meaning a value that is 37.5 mg/dL higher than the standard hypoglycemic threshold of 70 mg/dL, or 107.5 mg/dL.

Similarly, an automated insulin delivery algorithm may request at most a certain amount of the user's basal profile for one hour, one embodiment this being 4 times the user's basal profile for one hour. This means that a recommendation for user action may only need to occur if there is a glucose increase that cannot be compensated by insulin increase by the algorithm. As a result, a value that is greater than the hyperglycemic threshold of 180 mg/dL by 4 times the standard quantity of impact of increased basal, or 4 times 37.5 mg/dL (150 mg/dL) higher than 180 mg/dL, may be the threshold in this embodiment. In this example, the value of the threshold would thus be 330 mg/dL.

The values that are recommended in this example can vary across a wide range. For instance, the 50% assumption of TDI basal-bolus split can be modified into 25%, or 75%, based on the expected patterns of user activity. Moreover, the duration of assumed insulin action by the algorithm can be modified from 1 hour to 30 minutes (initial delay before insulin generally begins to take action), or 90 minutes (general insulin peak action time).

In another alternative exemplary embodiment, the clinical decision support algorithm defines the thresholds of action differently. The quantity of remaining insulin action may be specified differently than the IOB, such as by utilizing actual insulin delivery histories. The expected limits of insulin delivery by the automated system can also be assessed differently, such as by running a significant amount of simulations and assessing a reasonable maximum and minimum limits of the algorithm delivery over 1 hour.

In another alternative embodiment, the clinical decision support algorithm can incorporate more predictions of future glucose trends based on utilization of a model of insulin-glucose dynamics, and alert the users if glucose concentration values are actually predicted to remain above target or below the hypoglycemic thresholds.

While the present invention has been described with reference to exemplary embodiments herein, it should be appreciated that various changes in form and detail may be made without departing from the intended scope of the present invention as defined in the appended claims.

The invention claimed is:

1. A device, comprising:
a communication interface with a glucose monitor for enabling glucose level readings of a user from the glucose monitor to be communicated to the device;
a storage for storing insulin delivery history and/or glucagon delivery history to the user and a carbohydrate ingestion history of the user;
a delivery device interface with a delivery device for delivery of the insulin and/or glucagon to the user; and
processing logic for:
  determining a required insulin on board (IOB) of the user to reach a target glucose level of the user given a current glucose level of the user;
  determining a current IOB of the user;
  calculating a difference between the required IOB of the user to reach the target glucose level and the current IOB of the user;
  where the difference is positive,
    determining a limit of device compensation as a maximum automated insulin action that may result from automated insulin deliveries by the device in a period in view of constraints;
    determining whether the limit of device compensation is enough to reach the target glucose level of the user given the current glucose level and the current IOB of the user;
    where it is determined that the limit of device compensation is not enough to reach the target glucose level of the user, determining a hyperglycemic action threshold as a sum of the hyperglycemic threshold and a maximum amount of a glucose level of the user that can be compensated by the device in a time period in view of the limit of device compensation for the time period,
    comparing the current glucose level of the user to the hyperglycemic action threshold; and
    where the current glucose level of the user is greater than the hyperglycemic action threshold, triggering a preventive measure to reduce the glucose level of the user.

2. The device of claim 1, wherein the device further comprises a video display and the preventive measure comprises output displayed on the video display.

3. The device of claim 1, wherein the device further comprises an audio output device and the preventive measure comprises audio output that is output via the audio output device.

4. The device of claim 1, wherein the device, in addition to generating an alert as part of the preventive measure alert, causes delivery of a bolus of insulin to the user from the delivery device as part of the preventive measure.

5. The device of claim 1, wherein the triggered preventive measure is delivery of a bolus of insulin from the delivery device.

6. The device of claim 1, wherein the processing logic comprises one of a microprocessor, a field gate programmable array (FPGA), an application specific integrated circuit (ASIC) or a controller integrated circuit.

7. A method performed by processing logic of a device, the method comprising:
receiving a glucose monitor reading of a current glucose level of a user;

determining a required insulin on board (IOB) of the user to reach a hypoglycemic glucose level of the user given a current glucose level of the user;

determining a current IOB of the user;

calculating a difference between the current IOB of the user and the required IOB of the user to reach the hypoglycemic glucose level;

where the difference is positive, determining a limit of device compensation as a minimum automated insulin action that may result from suspension of automated insulin deliveries by the device in a period and/or automated glucagon deliveries by the device;

determining whether the limit of device compensation is enough to prevent the glucose level of the user from reaching the hypoglycemic glucose level given the current glucose level of the user and the current IOB of the user;

where it is determined that the limit of device compensation is not enough to prevent the glucose level of the user from reaching the hypoglycemic glucose level, determining a hypoglycemic action threshold as a sum of the hypoglycemic glucose level and a maximum amount of glucose level decrease that can be compensated for by insulin delivery suspension and/or automated glucagon delivery by the device over the time period;

comparing the current glucose level of the user to the hypoglycemic action threshold; and where the current glucose level of the user falls below the hypoglycemic action threshold, triggering an action to increase the glucose level of the user.

8. The method of claim 7, wherein the action comprises, with the device, causing the delivery of a bolus of glucagon to the user by the device and/or generating an alert that hypoglycemia may occur.

9. The method of claim 7, wherein the processing logic implements a closed loop control system for regulating delivery of glucagon to the user.

10. A non-transitory computer-readable storage media storing instructions that cause a processor to:

receive a glucose monitor reading of a glucose level of a user;

determine a required insulin on board (IOB) of the user to reach a hypoglycemic glucose level of the user given a current glucose level of the user;

determine a current IOB of the user;

calculate a difference between the current IOB of the user and the required IOB of the user to reach the hypoglycemic glucose level;

where the difference is positive, determine a limit of device compensation as a minimum automated insulin action that may result from suspension of automated insulin deliveries by the device in a period and/or automated glucagon deliveries by the device;

determine whether the limit of device compensation is enough to prevent the glucose level of the user from reaching the hypoglycemic glucose level given the current glucose level and the current IOB of the user;

where it is determined that the limit of device compensation is not enough to prevent the glucose level of the user from reaching the hypoglycemic glucose level, determine a hypoglycemic action threshold as a sum of the hypoglycemic glucose level and a maximum amount of glucose level decrease that can be compensated for by insulin delivery suspension and/or automated glucagon delivery by the device over the time period;

compare the current glucose level of the user to the hypoglycemic action threshold; and where the current glucose level of the user falls below the hypoglycemic action threshold, trigger an action to increase the glucose level of the user.

11. The non-transitory computer-readable storage media of claim 10, wherein the action comprises, with the device, causing the delivery of a bolus of glucagon to the user by a delivery device and/or generating an alert that hypoglycemia may occur.

12. The non-transitory computer-readable storage media claim 10, wherein the processor implements a closed loop control system for regulating delivery of glucagon to the user.

* * * * *